United States Patent
Gilmanshin et al.

(12)

(10) Patent No.: US 6,263,286 B1
(45) Date of Patent: Jul. 17, 2001

(54) METHODS OF ANALYZING POLYMERS USING A SPATIAL NETWORK OF FLUOROPHORES AND FLUORESCENCE RESONANCE ENERGY TRANSFER

(75) Inventors: Rudolf Gilmanshin, Waltham; Eugene Y. Chan, Boston, both of MA (US)

(73) Assignee: U.S. Genomics, Inc., Woburn, MA (US)

( * ) Notice: Subject to any disclaimer, the term of this patent is extended or adjusted under 35 U.S.C. 154(b) by 0 days.

(21) Appl. No.: 09/374,902

(22) Filed: Aug. 13, 1999

Related U.S. Application Data

(60) Provisional application No. 60/096,543, filed on Aug. 13, 1998.

(51) Int. Cl.$^7$ .............................. G01N 33/48; C12Q 1/68
(52) U.S. Cl. .................................... 702/19; 435/6
(58) Field of Search .................................. 435/6; 702/19

(56) References Cited

U.S. PATENT DOCUMENTS

| | | | |
|---|---|---|---|
| 4,962,037 | 10/1990 | Jett et al. | 435/6 |
| 4,979,824 | 12/1990 | Mathies et al. | 356/318 |
| 5,219,726 | 6/1993 | Evans | 435/6 |
| 5,374,527 | 12/1994 | Grossman | 435/6 |
| 5,404,320 | 4/1995 | Butler | 364/604 |
| 5,591,578 | 1/1997 | Meade et al. | 435/6 |
| 5,674,743 | 10/1997 | Ulmer | 435/287.2 |
| 5,807,677 | 9/1998 | Eigen et al. | 435/6 |
| 5,846,727 | 12/1998 | Soper et al. | 435/6 |

FOREIGN PATENT DOCUMENTS

| | | |
|---|---|---|
| WO 94/16313 | 7/1994 | (WO) . |
| WO 96/06189 | 2/1996 | (WO) . |
| WO 98/10097 | 3/1998 | (WO) . |
| WO 98/18965 | 5/1998 | (WO) . |
| WO 98/35012 | 8/1998 | (WO) . |

OTHER PUBLICATIONS

Alivisatos, 1996, "Perspectives on the Physical Chemistry of Semiconductor Nanocrystals", J. Phys. Chem. 100:13226–13239.

Bains, 1992, "Setting a Sequence to Sequence a Sequence", Bio/Technology 10:757–758.

Bruchez et al., 1998, "Semiconductor Nanocrystals as Fluorescent Biological Labels", Science 281:2013–2016.

Buckle et al., 1996, "Structural and Energetic Responses to Cavity–Creating Mutations in Hydrophobic Cores: Observation of a Buried Water Molecule and the Hydrophilic Nature of Such Hydrophobic Cavities", Biochem. 35:4298–4305.

Burns et al., 1998, "An Integrated Nanoliter DNA Analysis Device", Science 282:484–487.

Bustamante, 1991, "Direct Observation and Manipulation of Single DNA Molecules using Fluorescence Microscopy", Annu. Rev. Biophys. Biophys. Chem. 20:415–446.

Castro and Shera, 1995, "Single–Molecule Electrophoresis", Anal. Chem. 67:3181–3186.

Chan and Nie, 1998, "Quantum Dot Bioconjugates for Ultrasensitive Nonisotopic Detection", Science 281:2016–2018.

de Prat–Gay, 1996, "Asssociation of Complementary Fragments and the Elucidation of Protein Folding Pathways", Protein Eng. 9:843–847.

Eigen and Rigler, 1994, "Sorting Single Molecules: Application to Diagnostics and Evolutionary Biotechnology", Proc. Natl. Acad. Sci. USA 91:5740–5747.

Elson and Magde, 1974, "Fluorescence Correlation Spectroscopy. I. Conceptual Basis and Theory", Biopolymers 13:1–27.

Gouaux, 1997, "Channel–Forming Toxins: Tales of Transformation", Curr. Opin. Struct. Biol. 7:566–573.

Harrison et al., 1992, "Capillary Electrophoresis and Sample Injection Systems Integrated on a Planar Glass Chip", Anal. Chem. 64:1926–1932.

Heiger et al., 1990, "Separation of DNA Restriction Fragments by High Performance Capillary Electrophoresis with Low and Zero Crosslinked Polyacrylamide using Continuous and Pulsed Electric Fields", J. Chromatog. 516:33–48.

Holland et al., 1998, "Synthesis of Macroporous Minerals with Highly Ordered Three–Dimensional Arrays of Spheroidal Voids", Science 281:538–540.

Holzwarth et al., 1989, "The Acceleration of Linear DNA During Pulsed–Field Gel Electrophoresis", Biopolymers 28:1043–1058.

Jacobson et al., 1995, "Fused Quartz Substrates for Microchip Electrophoresis", Anal. Chem. 67:2059–2063.

Jameson and Eccleston, 1997, "Fluorescent Nucleotide Analogs: Synthesis and Applications", Meth. Enzymol. 278:363–390.

Kim and Baldwin, 1990, "Intermediates in the Folding Reactions of Small Proteins", Annu. Rev. Biochem. 59:631–660.

Kwiatkowski et al., 1994, "Solid–Phase Synthesis of Chelate–Labeled Oligonucleotides: Application in Triple–Color Ligase–Mediated Gene Analysis", Nucl. Acids Res. 22:2604–2611.

(List continued on next page.)

Primary Examiner—John S. Brusca
Assistant Examiner—Jeffrey S. Lundgren
(74) Attorney, Agent, or Firm—Pennie & Edmonds LLP

(57) ABSTRACT

The present invention relates to methods and apparatuses for analyzing molecules, particularly polymers, and molecular complexes with extended or rod-like conformations. In particular, the methods and apparatuses are used to identify repetitive information in molecules or molecular ensembles, which is interpreted using an autocorrelation function in order to determine structural information about the molecules. The methods and apparatuses of the invention are used for, inter alia, determining the sequence of a nucleic acid, determining the degree of identity of two polymers, determining the spatial separation of specific sites within a polymer, determining the length of a polymer, and determining the velocity with which a molecule penetrates a biological membrane.

67 Claims, 9 Drawing Sheets

OTHER PUBLICATIONS

Figure 1A:
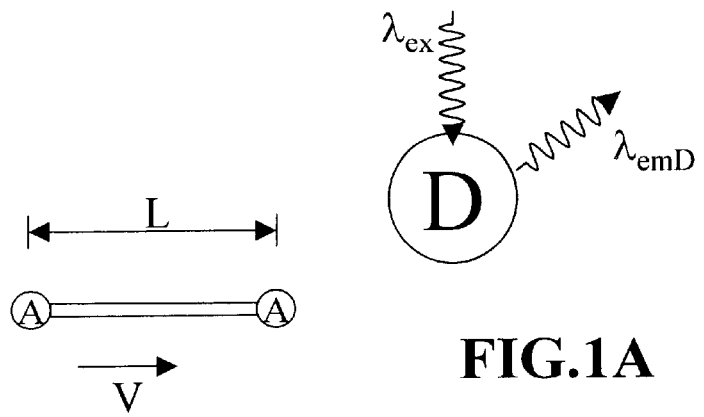

Langer et al., 1981, "Enzymatic Synthesis of Biotin–Labeled Polynucleotides: Novel Nucleic Acid Affinity Probes", Proc. Natl. Acad. Sci. USA 78:6633–6637.

Magde et al., 1974, "Fluorescence Correlation Spectroscopy. II. An Experimental Realization", Biopolymers 13:29–61.

Maxam and Gilbert, 1977, "A New Method for Sequencing DNA", Proc. Natl. Acad. Sci. USA 74:560–564.

Mullikin and McMurray, 1999, "Techview: DNA Sequencing. Sequencing the Genome, Fast", Science 283:1867–1869.

Ørum et al., 1995, "Sequence–Specific Purification of Nucleic Acids by PNA–Controlled Hybrid Selection", BioTechniques 19:472–480.

Rigler et al., 1993, "Fluorescence Correlation Spectroscopy with High Count Rate and Low Background: Analysis of Translational Diffusion", Eur. Biophys. J. 22:169–175.

Saha et al., 1993, "Time–Resolved Fluorescence of a New Europium Chelate Complex: Demonstration of Highly Sensitive Detection of Protein and DNA Samples", J. Am. Chem. Soc. 115:11032–11033.

Sanger et al., 1977, "DNA Sequencing with Chain–Terminating Inhibitors", Proc. Natl. Acad. Sci. USA 74:5463–5467.

Schwille et al., 1997, "Dual–Color Fluorescence Cross–Correlation Spectroscopy for Multicomponent Diffusional Analysis in Solution", Biophys. J. 72:1878–1886.

Seiler et al., 1993, "Planar Glass Chips for Capillary Electrophoresis: Repetitive Sample Injection, Quantitation and Separation Efficiency", Anal. Chem. 65:1481–1488.

Selvin, 1995, "Fluorescence Resonance Energy Transfer", Meth. Enzymol. 246:300–334.

Selvin et al., 1994, "Luminescence Resonance Energy Transfer", J. Am. Chem. Soc. 116:6029–6030.

Selvin and Hearst, 1994, "Luminescence Energy Transfer Using a Terbium Chelate: Improvements on Fluorescence Energy Transfer", Proc. Natl. Acad. Sci. USA 91:10024–10028.

Service, 1998, "Microchip Arrays Put DNA on the Spot" and "Coming Soon: the Pocket DNA Sequence", Science 282:396–399 and 399–401.

Shera et al., 1990, "Detection of Single Fluorescent Molecules", Chem. Phys. Lett. 174:553–557.

Sinclair, 1999, "Sequence or Die: Automated Instrumentation for the Genome Era", The Scientist 13:18–20.

Strezoska et al., 1991, "DNA Sequencing by Hybridization: 100 Bases Read by a Non–Gel–Based Method", Proc. Natl. Acad. Sci. USA 88:10089–10093.

Stryer, 1978, "Fluorescence Energy Transfer as a Spectroscopic Ruler", Annu. Rev. Biochem. 47:819–846.

Sung and Park, 1996, "Polymer Translocation Through a Pore in a Membrane", Phys. Rev. Lett. 77:783–788.

Tan and Kopelman, 1996, "Nanoscopic Imaging and Sensing by Near Field Optics", in: *Fluorescence Imaging Spectroscopy and Microscopy*, Wang and Herman, eds., John Wiley & Son, Chem. Anal. Ser. 137:407–475.

Waggoner, 1995, "Covalent Labeling of Proteins and Nucleic Acids with Fluorophores", Meth. Enzymol. 246:362–373.

Weiss, 1999, "Fluorescence Spectroscopy of Single Biomolecules", Science 283:1676–1683.

Wijnhoven and Vos, 1998, "Preparation of Photonic Crystals Made of Air Spheres in Titania", Science 281:802–804.

Williams et al., 1998, "Partition and Permeation of Dextran in Polyacrylamide Gel", Biophys. J. 75:493–502.

Woolley and Mathies, 1994, "Ultra–High–Speed DNA Fragment Separations Using Microfabricated Capillary Array Elecrophoresis Chips", Proc. Natl. Acad. Sci. USA 91:11348–11352.

Wu and Brand, 1994, "Resonance Energy Transfer: Methods and Applications", Anal. Biochem. 218:1–13.

Yang and Millar, 1997, "Fluorescence Resonance Energy Transfer as a Probe of DNA Structure and Function", Meth. Enzymol. 278:417–444.

Young and Anderson, 1985, "Quantitative Analysis of Solution Hybridisation", in: *Nucleic Acid Hybridization: A Practical Approach*, Hames and Higgins, eds., IRL Press, pp. 47–71.

Ha et al., "Probing the interaction between two single molecules: Fluorescence resonance energy transfer between a single donor and a single acceptor" Proc. Natl. Acad. Sci. USA 93, pp. 6264–6268, 1996.*

Sambrook et al., "Molecular Cloning: A Laboratory Manual" Cold Springs Harbor Laboratory Press, 1989.*

Lakowicz "Principles of Fluorescence Spectroscopy: Chapter 10" Plenum Press, New York 1983.*

* cited by examiner

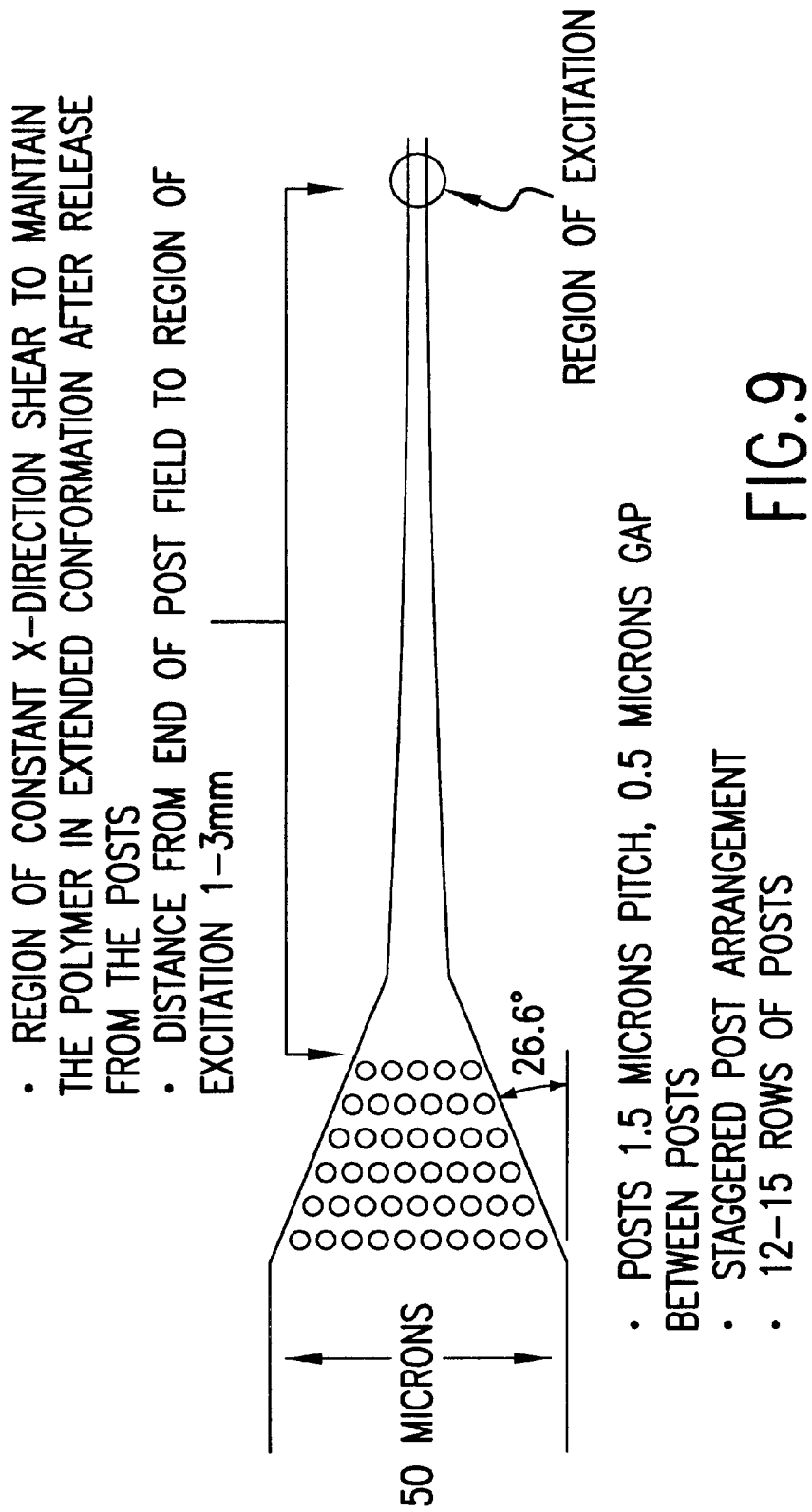

METHODS OF ANALYZING POLYMERS USING A SPATIAL NETWORK OF FLUOROPHORES AND FLUORESCENCE RESONANCE ENERGY TRANSFER

This application claims the benifit of to U.S. Provisional Application Ser. No. 60/096,543, filed Aug. 13, 1998, which is incorporated by reference herein in its entirety.

1. FIELD OF THE INVENTION

The present invention relates to methods and apparatuses for analyzing molecules, particularly polymers, and molecular complexes with extended or rod-like conformations. In particular, the methods and apparatuses are used to identify repetitive information, e.g., sequence information, in molecules or molecular ensembles, which is subsequently used to determine structural information about the molecules. The methods are based on the use of an autocorrelation function to identify common information in multiple molecules having at least one overlapping repetitive sequence.

2. BACKGROUND OF THE INVENTION

Macromolecules are involved in diverse and essential functions in living systems. The ability to decipher the functions, dynamics, and interactions of macromolecules is dependent upon an understanding of their chemical and three-dimensional structures. These three aspects—chemical and three-dimensional structures and dynamics—are interrelated. For example, the chemical composition of a protein, and more particularly the linear arrangement of amino acids, explicitly determines the three-dimensional structure into which the polypeptide chain folds after biosynthesis (Kim & Baldwin (1990) Ann. Rev. Biochem. 59: 631–660), which in turn determines the interactions that the protein will have with other macromolecules, and the relative mobilities of domains that allow the protein to function properly.

Biological macromolecules are either polymers or complexes of polymers. Different types of macromolecules are composed of different types of monomers, i.e., twenty amino acids in the case of proteins and four major nucleobases in the case of nucleic acids. A wealth of information can be obtained from a determination of the linear, or primary, sequence of the monomers in a polymer chain. For example, by determining the primary sequence of a nucleic acid, it is possible to determine the primary sequences of proteins encoded by the nucleic acid, to generate expression maps for the determination of mRNA expression patterns, to determine protein expression patterns, and to understand how mutations in genes correspond to a disease state. Furthermore, the characteristic pattern of distribution of specific nucleobase sequences along a particular DNA polymer can be used to unequivocally identify the DNA, as in forensic analysis.

In general, DNA identification and sequencing has been performed using methods, such as those described by Maxam and Gilbert (Maxam & Gilbert (1977) Proc. Natl. Acad. Sci. U.S.A. 74: 560–564) and by Sanger (Sanger et al. (1977) Proc. Natl. Acad. Sci. U.S.A. 74: 5463–5467) that determine the exact sequence of relatively short pieces of DNA. There are also techniques that arrange these short DNA fragments of known sequence in the proper order to obtain a longer sequence, such as those described by Evans (U.S. Pat. No. 5,219,726). Other methods of nucleic acid detection and sequencing have been developed, however, these too have limitations in the number of nucleotides they can read, in their abilities to resolve the identities of adjacent nucleotides, and in the practicality of their implementation.

Several methods for rapid sequencing of nucleic acids have been developed that use exonucleases to cleave individual bases from the nucleic acid polymer, which are subsequently identified in order to generate the sequence of the nucleic acid. U.S. Pat. No. 4,962,037 discloses a method wherein the nucleic acid fragment is suspended in a flowing stream while an exonuclease sequentially cleaves individual bases from the end of the fragment. The flowing stream delivers the cleaved bases in an ordered fashion to a detector for subsequent identification. A similar approach with some modifications is disclosed in U.S. Pat. No. 5,674,743. In this method, the DNA strand to be sequenced is processed with an exonuclease to cleave bases from the strand, and each cleaved base is then transported away from the strand and is incorporated into a fluorescence-enchancing matrix. In a particular embodiment, the intrinsic fluorescence of the nucleotide is induced and is used to identify it. Using a processive exonuclease, it is theoretically possible to sequence 10,000 bases or more at a rate of 10 bases per second. However, exonuclease sequencing has encountered many problems. If extrinsic labels are used to identify each base, all four bases must be tagged with, e.g., different fluorophores, which is sterically difficult; in addition, introduction of fluorophores may interfere with the enzymatic activity of the exonuclease. Furthermore, difficult optical trapping is needed to suspend DNA molecules in a flowing stream. Lastly, single molecules of fluorophore need to be detected with high efficiency, and only 95% efficiency has been achieved.

Methods of nucleic acid sequencing by hybridization with a specific set of oligonucleotide probes are also known in the art (Strezoska et al. (1991) Proc. Natl. Acad. Sci. U.S.A. 88: 10089–10093; Bains (1992) BioTechnology 10: 757–758). Although this approach is very costly to set up, sequencing by these methods is ultimately low-cost ($0.03–0.08 per base). Another advantage is the potential integration of the technique with microelectronics using special microchips for sequencing of nucleic acids fragments and even analysis of entire genomes (Service (1998) Science 282: 396–399 & 399–401). Traditional sequencing by hybridization techniques have the limitation of imperfect hybridization, especially under conditions in which hybridization is not favored, e.g., low-salt, or upon formation of secondary structure in the target nucleic acid, which interferes with binding to the probes. Imperfect hybridization leads to difficulties in generating adequate sequence because the error in hybridization is amplified many times.

U.S. Pat. No. 5,846,727 discloses a microsystem for rapid DNA sequencing in which a DNA template is amplified using the polymerase chain reaction ("PCR") and the PCR products are labeled and immobilized on a capillary tube wall. Then, Sanger extension products of the amplified DNA are prepared, labeled, and electrophoretically separated in a capillary channel. Near-infrared, laser-induced fluorescence of the oligonucleotides is detected. The same fluorophore is used to label all bases; however, different bases can be distinguished by difference of the fluorescence lifetimes induced by different bases upon the labeling. The substrate used is selected for compatibility with both the solutions and the conditions to be used in analysis, including but not limited to extremes of salt concentrations, acid or base concentration, temperature, electric fields, and transparence to wavelengths used for optical excitation or emission. The substrate material may include those associated with the semiconductor industry, such as fused silica, quartz, silicon, or gallium arsenide, or inert polymers such as polymethylmetacrylate, polydimethylsiloxane, polytetrafluoroethylene, polycarbonate, or polyvinylchloride. Because of its transmissive properties across a wide range of wavelengths, quartz is a preferred embodiment.

The use of quartz as a substrate with an aqueous solution means that the surface in contact with the solution has a positive charge. When working with charged molecules, especially under electrophoresis, it is desirable to have a neutral surface. In one embodiment, a coating is applied to the surface to eliminate the interactions which lead to the charge. The coating may be obtained commercially (capillary coatings by Supelco, Bellafonte Pa.), or it can be applied by the use of a silane with a functional group on one end. The silane end will bond effectively irreversibly with the glass, and the functional group can react further to make the desired coating. For DNA, a silane with polyethyleneoxide effectively prevents interaction between the polymer and the walls without further reaction, and a silane with an acrylamide group can participate in a polymerization reaction to create a polyacrylamide coating which not only does not interact with DNA, but also inhibits electro-osmotic flow during electrophoresis.

The microchannels may be constructed on the substrate by any number of techniques, many derived from the semiconductor industry, depending on the substrated selected. These techniques include, but are not limited to, photolithography, reactive ion etching, wet chemical etching, electron beam writing, laser or air ablation, LIGA, and injection molding. A variety of these techniques applied to polymer-handling chips have been discussed in the literature including by Harrison et al. (Analytical Chemistry 1992 (64) 1926–1932), Seiler et al. (Analytical Chemistry 1993 (65) 1481–1488), Woolley et al. (Proceedings of the National Academy of Sciences November 1994 (91) 11348–11352), and Jacobsen et al. (Analytical Chemistry 1995 (67) 2059–2063). The disclosed microsystem offers several advantages like the need of only sub-microliter volumes of expensive reagents, the ability to automate the procedure and perform several analyses simultaneously, and the use of a "highly efficient base-calling scheme using a single lane, single-dye format". Despite these advantages, typical read lengths of this method are still only on the order of 400–500 bases.

There are several other methods (U.S. Pat. No. 4,962,037 and U.S. Pat. No. 5,674,743, see below) that can be used to sequence long DNA molecules. However, the maximal length of a single DNA fragment that can be sequenced by existing techniques is still less than 2,000 bases (Mullikin & McMurray (1999) Science 283: 1867–1868; Sinclair (1999) The Scientist 15 (9): 18–20).

Methods have also been developed for quantitative detection of macromolecules in a sample. Recent developments in experimental techniques and available hardware have increased dramatically the sensitivity of detection so that optical measurements can be made of even single molecules in a sample. Such measurements can be done in aqueous solution, at room temperature (Weiss (1999) Science 283: 1676–1683), and in very small volumes to reduce background scattering.

Fluorescence correlation spectroscopy ("FCS") uses an autocorrelation function to process fluctuations in fluorescence emission from a restricted volume (Elson & Magde (1974) Biopolymers 13:1–27). This approach is essentially based on the assumptions that: (a) one or zero fluorescent molecules can be within an illuminated volume; and (b) the fluorescence emitted by the fluorescent molecule in the illuminated volume noticeably exceeds background. The detected fluorescent bursts, whose lengths are related to the time a molecule spends within the illuminated volume, can be used to identify and count molecules, as well as to determine diffusion coefficients (U.S. Pat. No. 4,979,824, WO Pat. No. 94/16313, the latter patent uses FCS).

Eigen & Rigler [(1994) Proc. Natl. Acad. Sci. U.S.A. 91: 5740–5747], describe the use of FCS for parallel screening of large amounts of genetic material for a particular sequence pattern. In particular, the interaction of a fluorescent ligand, e.g., a labeled oligonucleolide, with a larger target DNA can be measured by the correlation function describing the diffusion of the free and bound ligand. An oligonucleotide hybridized with a large DNA fragment would diffuse more slowly than free oligonucleotide, and therefore, the bound form of the fluorescent oligonucleotide exhibits longer photon bursts. A modification of this technique uses the cross correlation of signals obtained from different oligonucleotides labeled with different fluorophores to detect the presence of different oligonucleotide sequences within a DNA target sample (Schwille et al. (1997) Biophys. J. 72: 1878–1886).

PCT Publication No. WO 98/10097 discloses a method and apparatus for detection of single molecules emitting two-color fluorescence and determination of molecular weight and concentration of the molecules. The method involves the labeling of individual molecules with at least two fluorescent probes. The velocity is determined by measuring the time required for the molecules to travel a fixed distance between two laser beams. Comparison of the molecule's velocity with that of standard species permits determination of the molecular weight of the molecule, which may be present in a concentration as small as one femtomolar. The accuracy of the technique is limited by the time the molecule under scrutiny spends traveling through the spot of the focused laser beam. The diameter of the laser beam is diffraction limited and exceeds 0.4 $\mu$m for visible light.

Castro and Shera [(1995) Anal. Chem. 67: 3181–3186] describe the use of single molecule electrophoresis (SME) for the detection and identification of single molecules in solution. The technique involves the determination of electrophoretic velocities by measuring the time required for individual molecules labeled with a single fluorophore to travel a fixed distance between two laser beams. This technique has been applied to DNA, to fluorescent proteins and to simple organic fluorophores. An advantage of SME over conventional zone electrophoresis is that SME is a continuous flow system that permits real-time analysis, which is important when sample concentration and/or composition changes with time. The disclosed system has disadvantages when applied to the detection of a specific DNA sequence within a large genomic background. If a single fluorescent probe complementary to the sequence of interest is used, it can bind non-specifically to other sequences in the genomic DNA, which results in detection of a false positive. Moreover, an unbound probe also produces a detectable signal that could be misinterpreted as the presence of the target sequence.

U.S. Pat. No. 5,807,677 discloses a method and device for direct identification of a specific target nucleic acid sequence having a low copy number in a test solution. This method involves the preparation of a reference solution of a mixture of different short oligonucleotides. Each oligonucleotide includes a sequence complementary to a section of the target sequence and is labeled with one or more fluorescent dye molecules. The reference solution is incubated with the test solution under conditions favorable to hybridization of the short oligonucleotides with the nucleic acid target. The target sequence is identified in the solution by detection of the nucleic acid strands to which one or more of the labeled oligonucleotides are hybridized. To amplify the fluorescence signal, a "cocktail" of different oligonucleotides are used which are capable of hybridizing with sequences adjacent to but not overlapping with the target sequence. The disadvantage of this method is that, in order to design probes of the proper sequence, the exact sequence of the target nucleic acid and surrounding sequences must be known.

PCT Publication No. WO 96/06189 describes a method for quantitative detection of oligonucleotides using capillary electrophoresis. Typically, capillary electrophoresis employs fused silica capillary tubes whose inner diameters are between about 10–200 microns, and which can range in length between about 5–100 cm or more. As the inner diameter of such a capillary is small, electric fields 10 to 100 times stronger than those applicable in conventional electrophoretic systems can be applied because of reduced Joule heating. This permits very high speeds and superior resolution. In the methods described in PCT Publication No. WO 96/06189, a fluorescently labeled peptide nucleic acid ranging in size from 5–50 monomers is hybridized to a DNA sample and capillary electrophoresis through a polyacrylamide gel is performed under denaturing conditions (7 M urea) where the PNA/DNA complex is stable. This method suffers from limited detection sensitivity and cannot be used to detect single copy genes in large genomes.

The existing methods for sequencing polymers and for detecting the presence of small amounts of specific polymers in a sample each have drawbacks. The major drawbacks of sequencing techniques are that they are slow, labor intensive, and have fairly short read lengths (under 2,000 bases for nucleic acid sequencing) and limited accuracy. The methods for detecting molecules in a sample have the drawbacks of lack of sensitivity, frequent occurrence of false positive results, and, in some cases, a requirement that the sequence of the molecule to be detected must already be known. Clearly, there is a need for faster, simpler, more reliable and more universally applicable methods of sequencing and of detecting copies of sequences in a sample in order to elucidate complex genetic function and diagnose diseases and genetic dysfunctions more rapidly and accurately.

Citation of a reference herein shall not be construed as indicating that such reference is prior art to the present invention.

3. SUMMARY OF THE INVENTION

In a first embodiment, the present invention relates to a method for analyzing an extended object comprising: (a) moving with respect to at least one station a plurality of similar extended objects that are each similarly labeled with at least two unit-specific markers to generate a plurality of object-dependent impulses as the labeled extended objects pass the station; (b) measuring the generated plurality of object-dependent impulses as a function of one or more system parameters; and (c) calculating an autocorrelation function of said object-dependent impulses, to analyze the extended object.

In a second embodiment, the present invention relates to a method for analyzing an extended object comprising calculating an autocorrelation function of object-dependent impulses.

In a third embodiment, the present invention relates to an article of manufacture comprising a lattice of spherical beads having a plurality of fixed stations with at least one fluorophore positioned at each fixed station.

In a fourth embodiment, the present invention relates to a system for analyzing an extended object labeled with at least two unit-specific markers comprising: a central processing unit; an input device for inputting a plurality of object-dependent impulses of an extended object; an output device; a memory; at least one bus connecting the central processing unit, the memory, the input device, and the output device; the memory storing a calculating module configured to calculate an autocorrelation function for said plurality of object-dependent impulses of said extended object input using said input device.

In a fifth embodiment, the present invention relates to a computer program product for use in conjunction with a computer, the computer program product comprising a computer readable storage medium and a computer program mechanism embedded therein, the computer program mechanism comprising a calculating module configured to calculate an autocorrelation function of a plurality of object-dependent impulses.

The methods, articles of manufacture, computer system, and computer program products of the invention are useful for analyzing polymers, particularly DNA.

4. BRIEF DESCRIPTION OF THE DRAWINGS

Figure 1B:
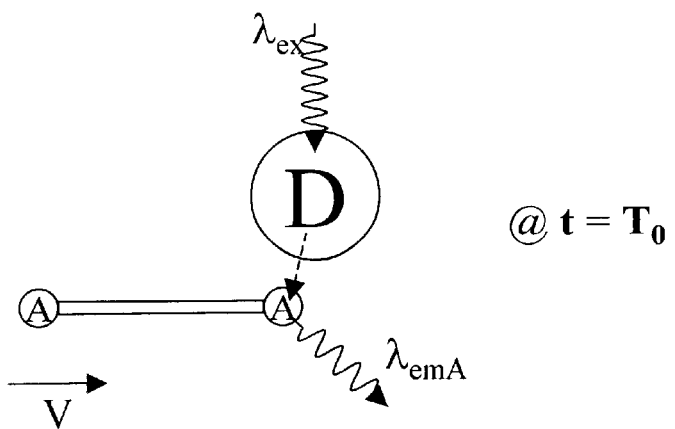
Figure 1C:
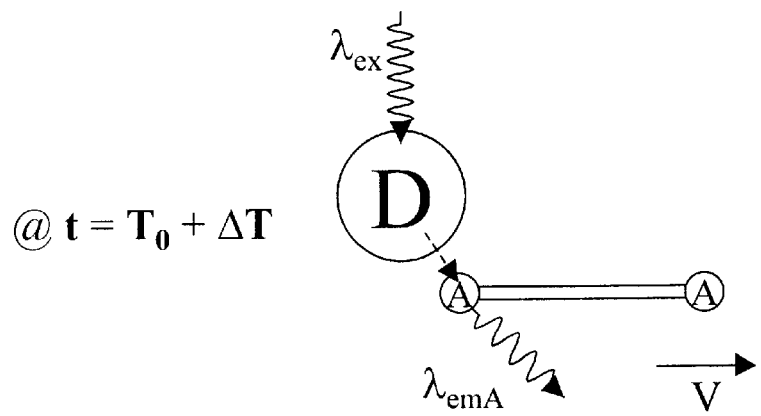

FIGS. 1A–1C. Outline of the method of correlated FRET. D and A are donor and acceptor fluorophores, respectively; L and V are length and velocity of movement of the labeled DNA fragment; $1_{ex}$, $1_{emD}$, and $1_{emA}$ are the wavelengths of the donor excitation, the donor emission, and the acceptor emission, respectively; $T_0$ and $T_0+\Delta T$ are the times when the first and the last acceptor fluorophores pass the D-center, respectively.

Figure 2:
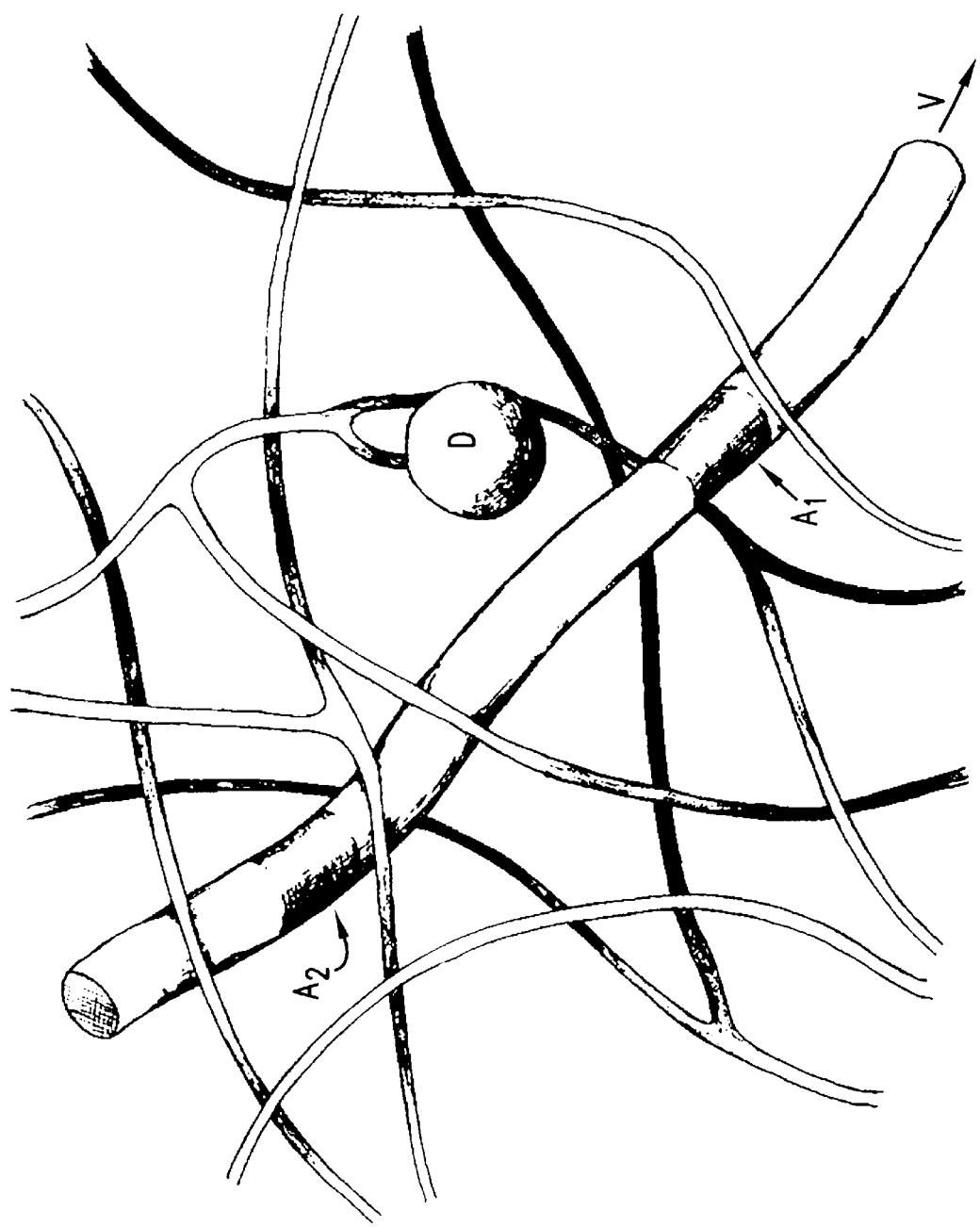

FIG. 2. A schematic diagram illustrating the restricted movement of an extended flexible molecule within a network.

Figure 3A:
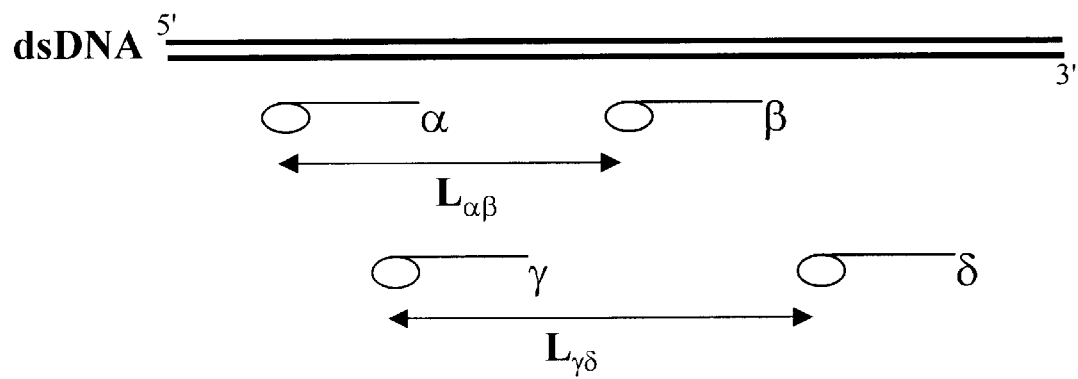
Figure 3B:
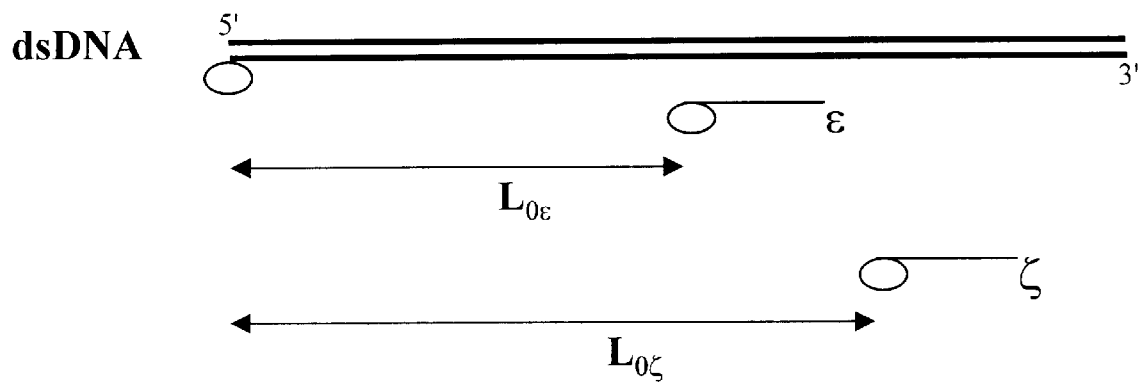

FIGS. 3A–3B. A schematic diagram depicting the hybridization sequencing with distance information: dsDNA is a double stranded DNA fragment to be sequenced; Greek letters denote probing oligonucleotides with fluorescence labels. Panel 3A: pairs of labeled probe oligomers are used in every run and $L_{ij}$ is the distance between the probes. Panel 3B: an end of the target DNA is labeled, a single labeled probe oligomer is used in every run and $L_{ij}$ is the distance between the labeled end of the DNA and the probe.

Figure 4:
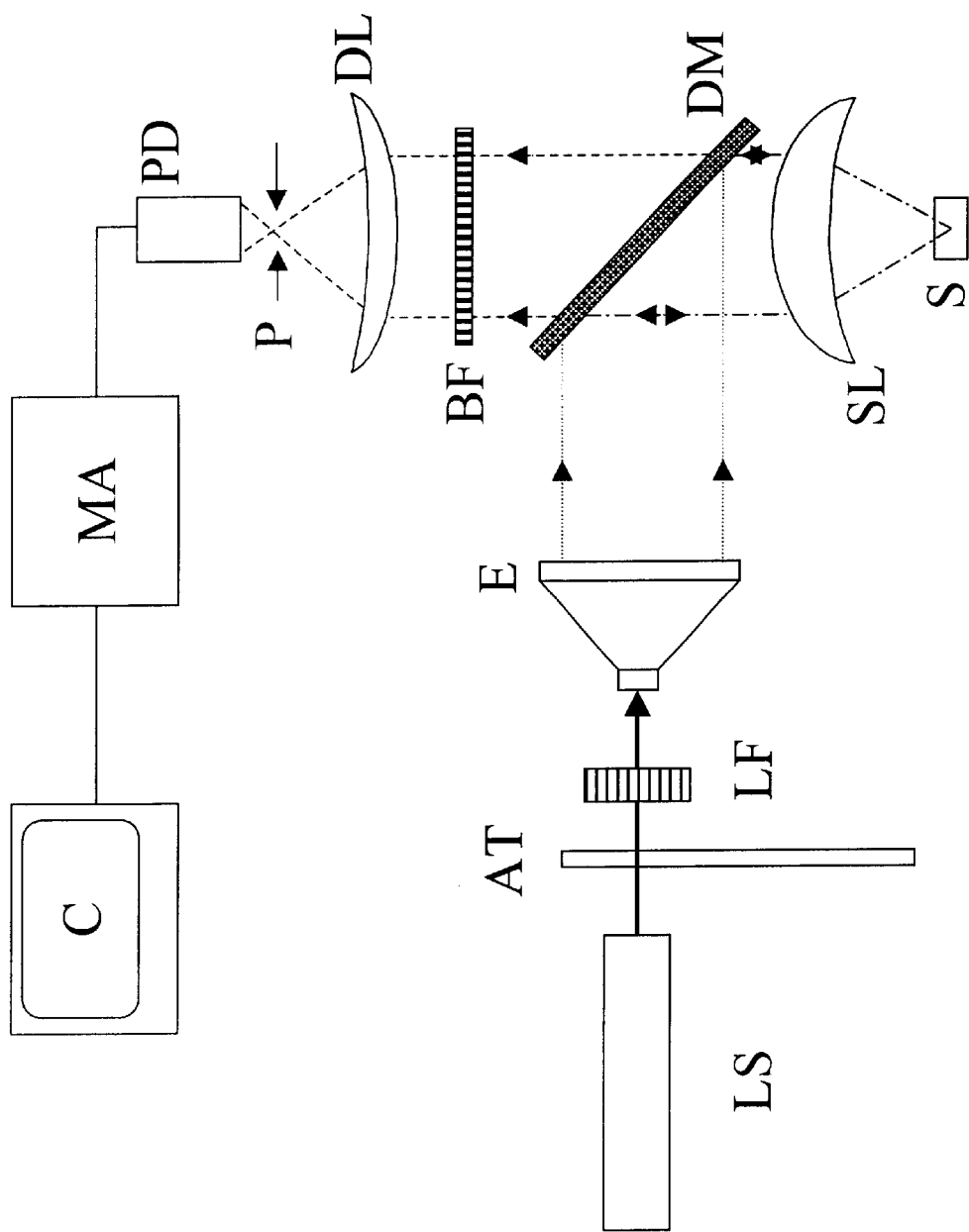

FIG. 4. An example of an optical setup for measurement of correlated FRET. L=laser; A=attenuator; LF=line filter; E=beam expander; DM=dichroic mirror; SL=sample lens; S=sample; DL=detector lens; BF=bandpass filter; P=pinhole; PD=photodetector; MA=multichannel analyzer; and C=computer.

Figure 5A:
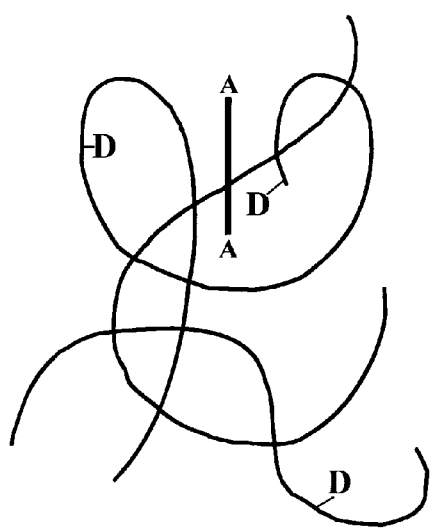
Figure 5B:
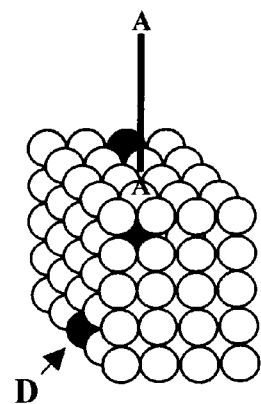
Figure 5C:
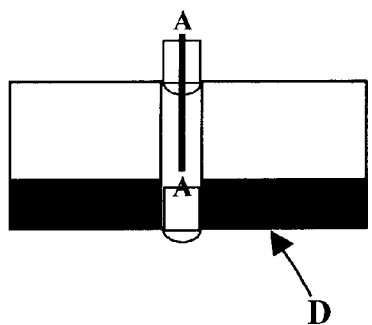

FIGS. 5A–5C. A schematic diagram of structures for performing the methods of analyzing extended objects using an autocorrelation function. Panel 5A: a gel matrix having D-centers bound within the matrix; Panel 5B: a lattice of spheres, wherein the D-centers are fluorescently labeled spheres; and Panel 5C: a nanochannel plate wherein the D-center is a thin film of donor fluorophores.

Figure 6:
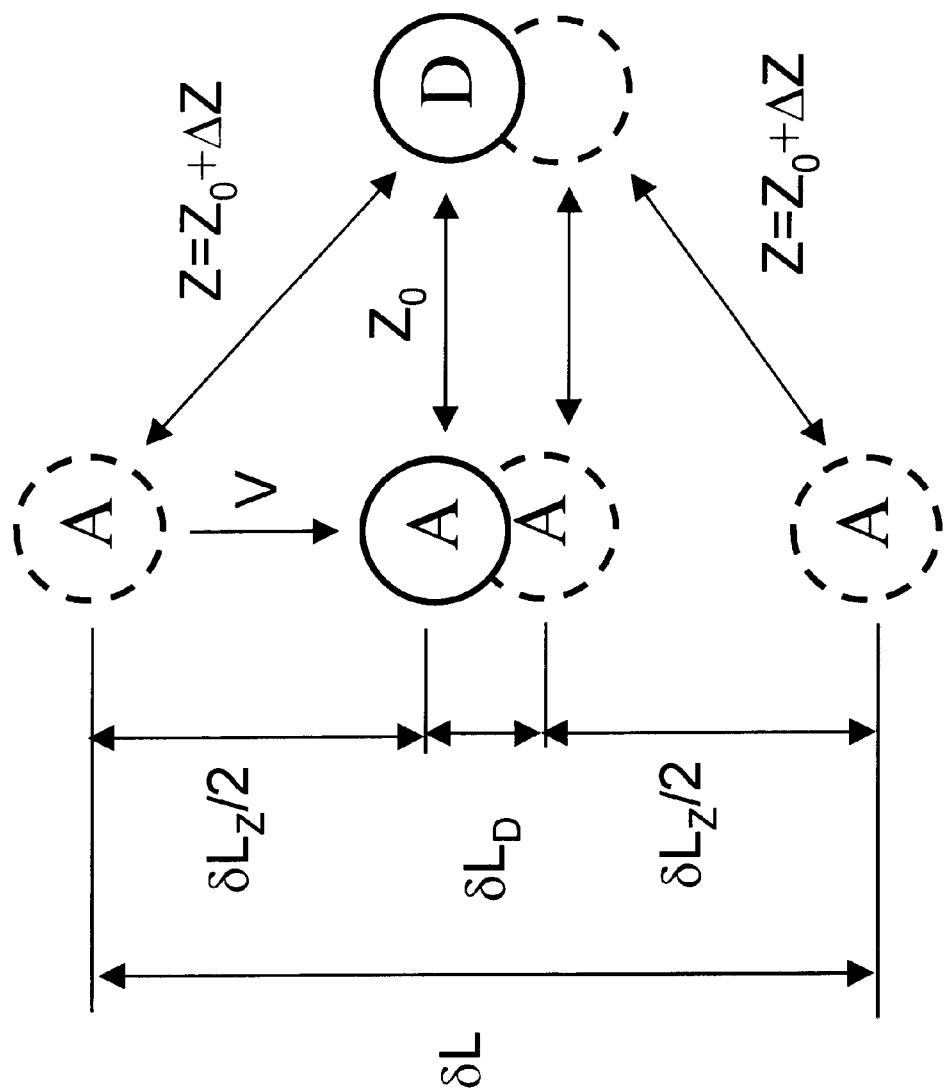

FIG. 6. A schematic diagram depicting the geometric limitations of the resolution of gel-bound D-centers.

Figure 7:
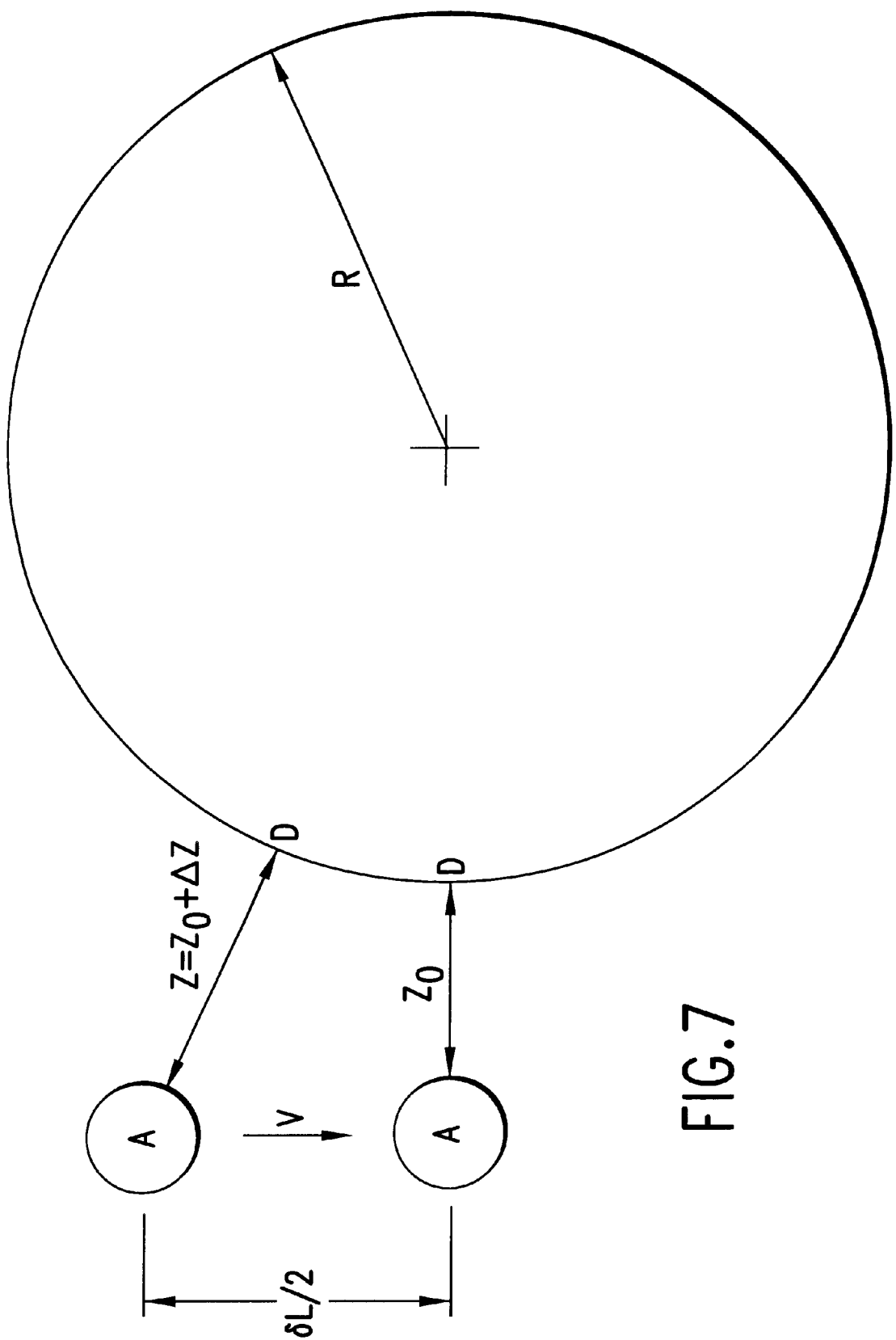

FIG. 7. A schematic diagram depicting the geometric limitations of the resolution of fluorescent beads as D-centers.

Figure 8:
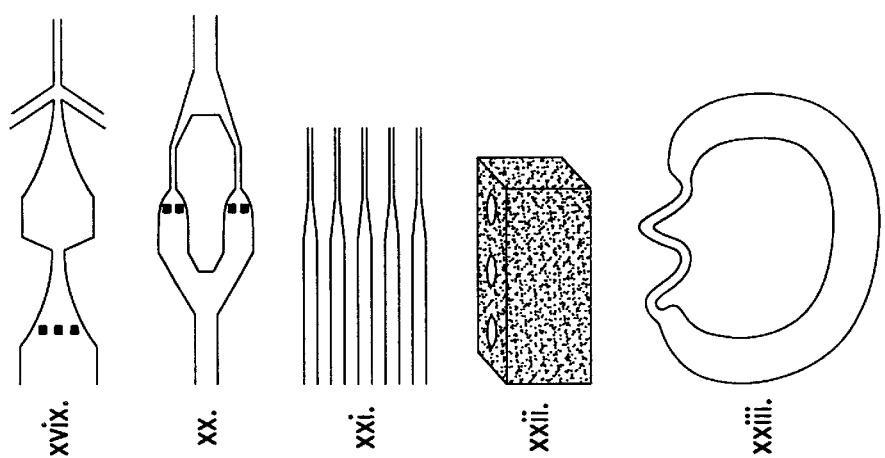
Figure 8:
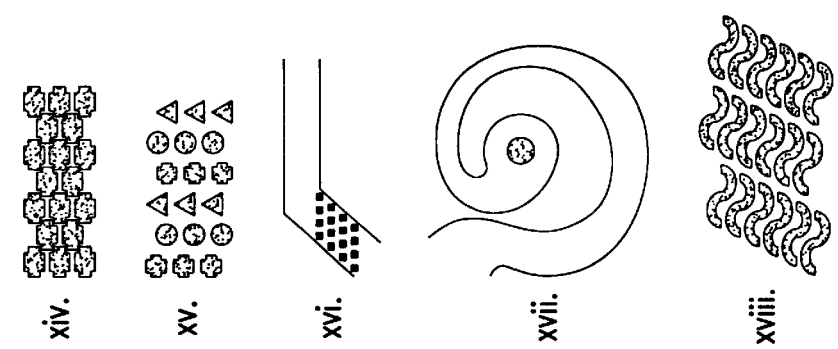
Figure 8:
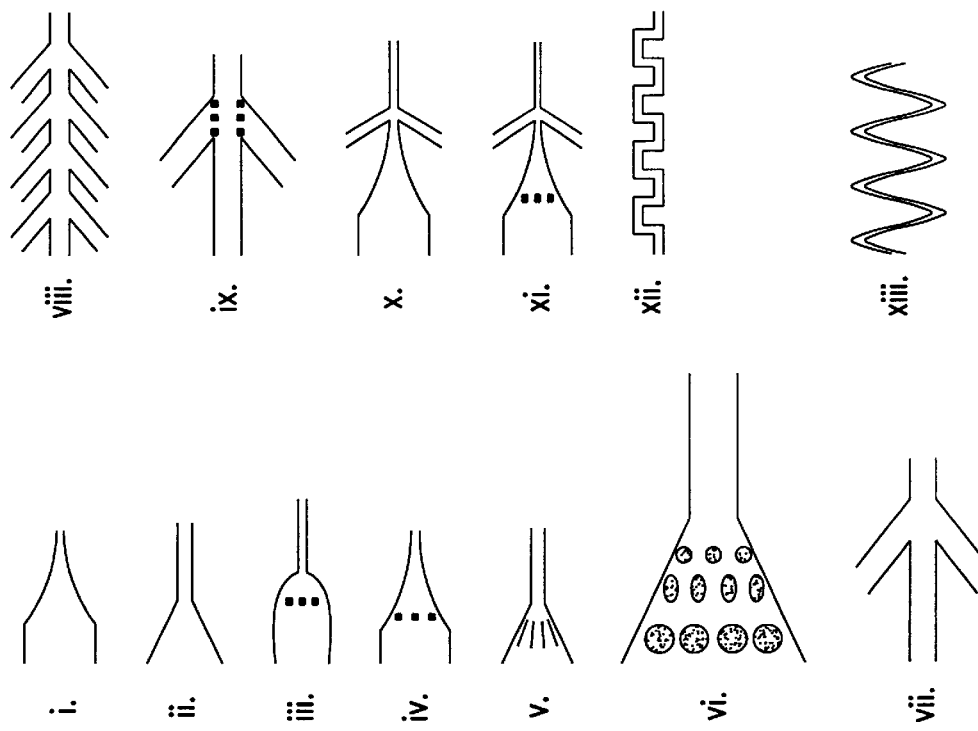

FIG. 8. shows examples of various structures that fall within the scope of the invention.

FIG. 9. shows a configuration for consistent unraveling, delivery, and stretching of DNA of varying sizes.

5. DETAILED DESCRIPTION OF THE INVENTION

5.1 Introduction

The present invention relates to methods of analyzing polymers as well as molecules and molecular complexes with extended or rod-like conformations. All objects to be analyzed are hereinafter referred to as "extended objects." In particular, the method is intended to identify repetitive information in the extended objects or in ensembles of extended objects. The extended objects are similar, or preferably, the same, and comprise a similar, or preferably, an identical pattern of labeled units. The labeled extended objects are moved past at least one station, at which labeled units of the extended objects interact with the station to produce an object-dependent impulse. Preferably, labeled extended objects are moved past a plurality of stations. Because the extended objects are similar, or preferably identical, and comprise a similar, or preferably, identical pattern of labeled units, a characteristic signature of interactions is repeated as each extended object moves past a station or a plurality of stations. This repetitive information is extracted from the overall raw data by means of an autocorrelation function and is then used to determine structural information about the extended objects. As used in this application, "moves past" refers to embodiments in which the station is stationary and the extended object is in motion, the station is in motion and the extended object is stationary, and the station and extended object are both in motion; all such embodiments are within the scope of the invention.

In the preferred embodiment, the extended object to be analyzed is a polymer. A polymer, as used herein, is a compound having a linear backbone of individual units linked together by covalent bonds. Preferably, the backbone is unbranched. The term "backbone" is given its usual meaning in the field of polymer chemistry. The polymers may be heterogeneous in backbone composition, thereby containing any possible combination of individual monomer units linked together, e.g., peptide-nucleic acids (PNA), having a polypeptide-like backbone, based on the monomer 2-aminoethyleneglycin carrying any of the four nucleobases: A, T, G, or C. In a preferred embodiment, the polymers are homogeneous in backbone composition and are, e.g., nucleic acids or polypeptides. A nucleic acid as used herein is a biopolymer comprised of nucleotides, such as deoxyribose nucleic acid (DNA) or ribose nucleic acid (RNA). A protein or polypeptide as used herein is a biopolymer comprised of amino acids. In the most preferred embodiment, the extended object is a double-stranded DNA molecule with a rigid structure.

As used herein with respect to individual units of a polymer, "linked" or "linkage" means two units are joined to each other by any physicochemical means. Any linkage known to those of ordinary skill in the art, covalent or non-covalent, is embraced. Natural linkages, e.g., amide, ester, and thioester linkages, which are those ordinarily found in nature to connect the individual units of a particular polymer, are most common. However, the individual units of a polymer analyzed by the methods of the invention may be joined by synthetic or modified linkages.

A polymer is made up of a plurality of individual units, which are building blocks or monomers that are linked either directly or indirectly to other building blocks or monomers to form the polymer. The polymer preferably comprises at least two chemically distinct linked monomers. The at least two chemically distinct linked monomers may produce or be labeled to produce different signals. Different types of polymers are composed of different monomers. For example, DNA is a biopolymer comprising a deoxyribose phosphate backbone to which are attached purines and pyrimidines such as adenine, cytosine, guanine, thymine, 5-methylcytosine, 2-aminopurine, hypoxantine, and other naturally and non-naturally occurring nucleobases, substituted and unsubstituted aromatic moieties. RNA is a biopolymer comprising a ribose phosphate backbone to which are attached purines and pyrimidines such as those described for DNA but wherein uracil is substituted for thymidine. Deoxyribonucleotides may be joined to one another via an ester linkage through the 5' or 3' hydroxyl groups to form the DNA polymer. Ribonucleotides may be joined to one another via an ester linkages through the 5', 3' or 2' hydroxyl groups. Alternatively, DNA or RNA units having a 5', 3' or 2' amino group may be joined via an amide linkage to other units of the polymer.

The polymers may be naturally-occurring or non-naturally occurring polymers. Polymers can be isolated, e.g., from natural sources using biochemical purification techniques. Alternatively, polymers may be synthesized, e.g., enzymatically by in vitro amplification using the polymerase chain reaction (PCR), by chemical synthesis, or by recombinant techniques.

The methods of the invention are performed by detecting signals referred to as object-dependent impulses. An "object-dependent impulse," as used herein, is a detectable physical quantity which transmits or conveys information about the structural characteristics of at least one unit-specific marker of an extended object. A unit-specific marker, as used herein, can either be a measurable intrinsic property of a particular type of individual unit of the extended object, e.g., the distinct absorption maxima of the naturally occurring nucleobases of DNA (the polymer is intrinsically labeled), or a compound having a measurable property that is specifically associated with one or more individual units of a polymer (the polymer is extrinsically labeled). A unit-specific marker of an extrinsically labeled polymer may be a particular fluorescent dye with which all nucleobases of a particular type, e.g., all thymine nucleobases, in a DNA strand are labeled. Alternatively, a unit-specific marker of an extrinsically labeled polymer may be a fluorescently labeled oligonucleotide of defined length and sequence that hybridizes to and therefore "marks" the complementary sequence present in a target DNA. Unit-specific markers may further include, but are not limited to, sequence specific major or minor groove binders and intercalators, sequence-specific DNA or peptide binding proteins, sequence specific PNAs, etc. The detectable physical quantity may be in any form which is capable of being measured. For instance, the detectable physical quantity may be electromagnetic radiation, chemical conductance, radioactivity, etc. The object-dependent impulse may arise from energy transfer, directed excitation, quenching, changes in conductance (resistance), or any other physical changes. Although an object-dependent impulse is specific for a particular unit-specific marker, an object comprising more than one unit-specific marker will have more than one identical object-dependent impulse. Additionally, chemically distinct unit-specific markers will give rise to different object-dependent impulses.

The method used for detecting the object-dependent impulse depends on the type of physical quantity generated. For instance, if the physical quantity is electromagnetic radiation, then the object-dependent impulse is detected optically. An "optically detectable" object-dependent impulse as used herein is a light-based electromagnetic radiation signal that can be detected by light detecting imaging systems. When the physical quantity is chemical conductance, then the object-dependent impulse is chemically detected. A "chemically detected" object-dependent impulse is a signal in the form of a change in chemical concentration or charge, such as ion conductance, which can be detected by standard means for measuring chemical potential or conductance. If the physical quantity is an electrical signal then the object-dependent impulse is in the form of a change in resistance or capacitance.

An object-dependent impulse arises from a detectable physical change in the unit-specific marker of the extended object, in the station, or in the environment surrounding the station. As used herein, a "detectable physical change" in the unit-specific marker or the station is any type of change that occurs in the unit-specific marker or the station as a result of exposing the unit-specific marker to the station. When the unit-specific marker is exposed to the station, a detectable signal is created. The station may be an interaction station or a signal generation station. The type of change that occurs in the station or in the unit-specific marker to produce the detectable signal depends on the type of station and unit-specific marker used. Several examples of combinations of station and unit-specific markers that produce detectable signals are discussed herein below. Those of skill in the art will be able to derive other combinations of stations and unit-specific markers that fall within the scope of the invention.

A "signal generation station" as used herein is a station that is an area where the unit-specific marker interacts with the station or the environment around the station to generate an object-dependent impulse. In one embodiment of the invention, the object-dependent impulse results from contact in a defined area with an agent selected from the group consisting of electromagnetic radiation, a quenching source, and a fluorescence excitation source which can interact with the unit-specific marker to produce a detectable signal. In another embodiment, the object-dependent impulse results from contact in a defined area with a chemical environment that is capable of undergoing specific changes in conductance in response to an interaction with a chemically distinct structure. As the chemically distinct structure interacts with the chemical environment, a unique change in conductance occurs. The structure-specific change may be temporal, e.g., the length of time required for the conductance to change, or it may be physical, e.g., the magnitude of an intensity change. In yet another embodiment, the object-dependent impulse results from changes in capacitance or resistance caused by the movement of the unit-specific marker between microelectrodes or nanoelectrodes positioned adjacent to the object. For example, the signal generation station may include microelectrodes or nanoelectrodes positioned on opposite sides of the object such that a particular change in conductance (resistance) that occurs as a result of the movement of a unit-specific marker past the electrodes will be specific for the particular unit-specific marker.

Although the scope of the invention encompasses the detection of any useful physical changes, it is preferable to detect particular types of physical changes. For example, it is most preferable to carry out the methods of the present invention at room temperature and with the extended object dissolved in a solvent. The scale of thermal fluctuations at 300 K (room temperature) is $\Delta E_T=1/40$ eV; therefore, the energy of an object-dependent impulse must considerably exceed this value in order to be resolved from the thermal noise. Therefore, optical detection is most preferable, as the energy of a photon with a wavelength in the visible light range is approximately 1 eV. Indeed, reliable detection of single photons by various means is well known in the art. In the case of changes in conductivity, the scale of the effect is determined by $\Delta E_C=q^2/2C$, where q is the charge transferred due to the object-dependent impulse and C is the capacitance of the electrodes used for the measurement. Using electron beam lithography, the electrodes can be manufactured as small as 30×30 nm$^2$, which corresponds to a capacitance of approximately $3\times10^{-17}$ F, and the thermal fluctuation amplitude at room temperature is equal to the transfer of 10 electrons. This limits the minimal change in ion concentration that must be measured by the electrodes in order to produce a signal that is detectable above background. Moreover, biomolecules are studied in buffered solutions, and the measurement of conductivity in a small volume of salt solution is additionally hindered by electrokinetic effects. In contrast, the major requirement for optical detection is that the surrounding media be optically transparent within the spectral range of detection. Therefore, a high energy per unit (photon) and the relative insensitivity to the properties of the surrounding media make optical changes the most preferred physical change to detect an object-dependent impulse.

Various methods and products are available for analyzing extended objects, as described in PCT Publication No. WO 98/35012, which is incorporated herein by reference in its entirety.

Various optical effects that can be measured differ in their potential sensitivity and resolution, i.e., the minimum distance between two objects wherein the objects are distinguishable. A low resolution corresponds to a larger distance between distinguishable objects; a high resolution corresponds to a smaller distance between distinguishable objects. The resolution of a particular technique is determined by the characteristic distance through which the station may sense the particular unit-specific marker of the extended object. A shorter characteristic distance makes for better resolution. The lowest resolution techniques include monitoring of light transmission and directed excitation. In the both cases, a source of light is employed, and it is the size of the light source that limits resolution. The minimum size of a light source used in near-field optics exceeds 10 nm, and the effective size of the source increases exponentially with the distance between the source and the object to be illuminated. Therefore, a resolution of 50–100 nm or more is known in the art (Tan & Kopelman (1996) Chem. Anal. Ser. 137: 407–475.). The resolution of quenching techniques is dictated by the size of the fluorophore that is in contact with the quencher. However, the signal change is detected on a "bright background," which decreases its sensitivity. Also, the quenching of a fluorophore by other components in the solution, its bleaching, or its transition to a long-lived triplet state is indistinguishable from its quenching. Finally, it is difficult to design an experimental set up wherein all unit-specific markers of the extended object have direct contact with the same quenching group, which limits the utility of a station comprising a contact quencher.

5.2 Correlated Fluorescence Resonance Energy Transfer

In a preferred embodiment, the object-dependent impulses produced by the interaction between the labeled units of the extended object and the station arise as a result of fluorescence resonance energy transfer ("FRET"). FRET occurs when two fluorophores are in close proximity and when the emission spectrum of one fluorophore, the donor D, overlaps with the excitation spectrum of the other fluorphore, the acceptor A, and when D is in an excited state. The rate of energy transfer $k_T$ is given by:

$$k_T = 1/\tau_D (Z_F/Z)^6 \quad (1)$$

where $\tau_D$ is the fluorescence lifetime of D, Z is the distance between D and A, and $Z_F$ is the Förster radius. When $Z=Z_F$, the rates of emission and energy transfer are equal, and 50% of excited donors are deactivated by energy transfer. The value of $Z_F$ is calculated from spectroscopic parameters of D and A and takes into account their relative orientation. The utility of FRET is derived from the strong dependence of the efficiency of energy transfer on the sixth power of the distance between D and A. The most efficient energy transfer occurs when the distance between D and A is close to $Z_F$, which is between two and seven nanometers for most organic fluorescent dye pairs (Wu & Brand (1994) Anal. Biochem. 218:1–13). Because of this strong distance dependence, FRET is often referred to as a "spectroscopic ruler" that is able to measure distances in the nanometer range (Stryer (1978) Ann. Rev. Biochem. 47:819–846).

In the methods of the present invention, FRET data is analyzed using an autocorrelation function. In one embodiment, the extended object is labeled with fluorescent donors D and the station is labeled with fluorescent acceptors A. In another embodiment, the extended object is labeled with fluorescent acceptors A and the station is labeled with fluorescent donors D. The movement of the extended object is such that each of the unit-specific markers (D or A) on the object is moved within the proper distance of the A or D at the station for FRET to occur. The Ds are illuminated with light at the wavelength of excitation of the donor. Emitted light is monitored within the wavelength band of emission of the As and includes background emission and photons emitted by the As due to FRET from the Ds.

The movement of the extended objects to be analyzed is dominant in the direction of the long axis of the extended object, while fluctuation in the plane perpendicular to the long axis is much smaller (FIG. 1A). For an extended object having multiple unit-specific markers, FRET from the unit-specific marker at the leading end of the object (FIG. 1B) is always followed by FRET from the unit-specific marker at the trailing end of the object (FIG. 1C) as each one passes a given station. For an extended object having one unit-specific marker FRET at the first station along the object's path is always followed by FRET at the second station along the object's path if: (a) one pair of stations is present and all objects are moving along the path of this pair of stations; or (b) there are many pairs of stations along the path of the extended objects and the inter-station distance is the same in all pairs of stations. Therefore, bursts of photons from these FRET events are correlated. This correlation allows the FRET events to be distinguished from background emission by means of an autocorrelation function. In a preferred embodiment, the autocorrelation function is defined by formula 2:

$$G(\tau) = 1/T \int_0^T I(t)I(t+\tau)\,dt \quad (2)$$

wherein $G(\tau)$ is the autocorrelation function of the measured embodiment-dependent time dependence of emission intensity $I(t)$, and T is the total time of measurement of $I(t)$. In its simplest form, when the photon counting mode is used, $I(t)$ has a value of one at the time when a photon is detected and is zero at other times. For background photons measured at time t, there may or may not be another photon at time $t+\tau$. Therefore, the product $I(t)I(t+\tau)$ may be either zero or one. At lower background levels, the proportion of zero products is greater. In contrast, for correlated events, a photon emitted at time t is always accompanied by a photon emitted at time $t+\tau_0$, where $\tau_0=L/V$, the interval of correlation wherein L is the distance between labels and V is the velocity of the extended object. The autocorrelation function $G(\tau)$ exhibits a maximum at $\tau=\tau_0$, the interval of correlation, and enables either L or V to be calculated, depending on which of these parameters is known. Although the autocorrelation function is discussed herein in relation to FRET analysis, one with skill in the art will recognize that this form of data analysis is applicable to other embodiments of the invention and that the autocorrelation function can be a function of one or more system parameters other than time.

One of skill in the art will recognize that although formula 2 is written for a continuous emission intensity I, the autocorrelation function may also be calculated for a discrete emission intensity:

$$G_j = (1/N) \sum_{i=0}^{N} I_i I_{i+j} \quad (3)$$

where $I_i$ corresponds to the moment $t_i$, $I_{i+j}$ corresponds to the moment $t_i + j\Delta t$, $G_j$ is the autocorrelation function at time $\tau = j\Delta t$, and N is the total number of data values in the $I(t)$ sequence.

The application of an autocorrelation function for data analysis removes volume and concentration restrictions from the experimental design. The volume of the experiment is only limited by the background emission generated using a particular experimental set up. The resolution of the method is determined by the scale on which the monitored interaction between station and object occurs, e.g., nm, $\mu$m, mm, cm, etc.

In a preferred embodiment, the fluorescence of D-centers is excited and fluorescence of As is measured. Therefore, in this embodiment, only the fluorescence occurring due to FRET is studied. The movement of extended objects is arranged so that all portions of each object follow approximately the same path. Since every object includes more than one unit-specific marker (A or D), each fluorescence emission arising from interaction of the first fluorophore of every object with a station is accompanied by the emission arising from interaction of the second fluorophore of every object with the station. Because all of the objects are identically (or similarly, as discussed below) labeled, the A or D groups are separated by the same distance. If the velocities of all of the extended objects are approximately the same, then the corresponding time intervals $\Delta T_i$ of different molecules will also be approximately the same, meaning that FRET events are correlated for the group of objects being analyzed. Therefore, the time $\Delta T$ can be determined by calculating the autocorrelation function $G(t)$ of the measured fluorescence time dependence, which will have a peak at $t=<\Delta T>$, where $<\Delta T>$ is an average value of all corresponding $\Delta T_i$ measured. The width of the peak at $t=<\Delta T>$ provides the width of the distribution of $\Delta T$ for the measured system.

The temporal resolution $\delta t$ of the measurement of the I(t) dependence should be $\leq 0.1\Delta T$ in order to obtain information about the distribution width of $\Delta T$ (variations in $\Delta T$ values for different molecules moving in the studied volume) in a real system. For very short DNA fragments of 10 base pairs (3.4 nm in length), the value of $\Delta T$ is on the order of $10^{-4}$ s for DNA moving at a velocity of $V=10^4$ nm/s, which is typical of standard electrophoresis conditions. For longer DNA fragments, the time will be proportionally longer. Hence, a time resolution of 1–10 microseconds is sufficient to analyze DNA.

The total time of measurement T depends upon the total number of correlated events that must be measured in order to obtain the desired S/N ratio. If the distribution width of $\Delta T$ is narrower than the time window of measurement, then $N_{corr} \geq 100$ correlated events are preferably measured so that $S/N \geq 10$. If the distribution width of $\Delta T$ is wider than the time window of measurement, more events should be measured to have the same S/N ratio at the maximum of $G(\tau)$.

It is not necessary to calculate the autocorrelation function $G(\tau)$ for the whole range $\delta t < t < T$. The range $\delta t < t < T_{eff} >> 10 \Delta T_{max}$ is sufficient to determine the time intervals $\Delta T \leq \Delta T_{max}$ where $\Delta T_{max}$ is the maximal interval for a given distribution of labels on the DNA sample. The expected resolution of the proposed systems (see below) is $\delta L = 10$ nm, which corresponds to the length of a DNA helix of 30 base pairs. Therefore, a dynamic range of $10^3$ (which means $10^3 \Delta T_{min} \geq \Delta T_{max}$) is sufficient to analyze DNA fragments of $10^4$ base pairs or shorter. The conditions $\delta t \leq 0.1 \Delta T_{min}$ and $T_{eff} = 10 \Delta T_{max}$ give minimal dynamic range $10^5$ for the I(t) measurement sufficient for the study of DNA fragments of $10^4$ base pairs or shorter at a given resolution. Integrators capable of measurement of 64,000 points per I(t) curve are commercially available. In one embodiment, a better S/N ratio, is obtained from many separately measured I(t) dependences (for the same system under the same conditions) of the minimal length $T_{eff}$ that are combined.

The peak width $\Delta \tau$ on the $G(\tau)$ at $\tau = \Delta T$ is determined by variation of the $\Delta T$ values for different molecules moving in a real system. The width $\Delta \tau$, which can be estimated from the width of a band on a polyacrylamide gel corresponding to a particular DNA fragment (see below), limits the maximal size of the DNA fragment that can be analyzed with this approach.

For example, if the first and last units of a 6-unit polymer are labeled, then a series of bursts of emitted photons will be detected arising from the polymers wherein the coupled bursts have a constant separation interval $\Delta T$ resulting from the photons emitted by the first and last labeled units on each polymer. Using the autocorrelation function to analyze this data set, the data are resolved from the multiple polymers to identify that there is a 6-unit spread between the first and second labels on the polymer. If it is known that the first and second labels on the polymer correspond to the first and last units of the polymer, then the autocorrelation analysis indicates that the polymer is 6 units long.

In one embodiment, the method of the invention is used to determine the velocities of penetration of objects, e.g., drugs, toxins, biopolymers, etc., through biological membranes or through protein channels. For example, the microscopic speed of transmembrane transport through a protein pore is determined by the method of the invention. Where a floating fluorophore is a donor and a pore-forming protein is labeled with acceptors, the situation is mathematically equivalent to that presented in FIGS. 1A–1C. Indeed, the two acceptor labels at either end of the pore are permanently separated by distance L and their velocity relative to the D-center is V, where V is the velocity of the floating fluorophore through the channel of the protein, and the floating D-center is always within the Förster distance of the channel walls. The distance L is often known from independent structural analysis (Gouaux (1997) Curr. Opin. Struct. Biol. 7:566–573) and so V is easily determined.

In another embodiment, the determined time interval $\Delta T$ separating the correlated events is used to calculate the distance between the labels when the velocity of the object is known, or vice versa. The velocity of an object as it moves past a station is easily determined. For instance, in one embodiment where the object is a DNA molecule, the velocity of a control DNA molecule of known length and sequence are measured. The ends of the control DNA molecule are labeled and the methods of invention are performed on the control molecule. Since the distance between labels on the control molecule is the length of the molecule, which is known in this embodiment, the autocorrelation function analysis determines the velocity of the DNA molecule based on the amount of time required for the two FRET events to occur that correspond to the ends of the molecule passing the station. Once the velocity of the control DNA molecule has been measured under a particular set of experimental conditions, the methods of the invention are subsequently used to determine the distance between two or more labels on an unknown DNA analyzed under the same general experimental conditions. Once the velocity of the unknown DNA molecule is known, the distance between two or more labels on the unknown molecule is determined.

In another embodiment, both the rate of movement of an experimental DNA molecule and the distance between two or more units or unit-specific markers in the same molecule are determined by using sets of acceptors that emit light at different wavelengths. The end units of the DNA molecule are labeled with one set of acceptors, which emit light at a first wavelength, and two or more internal units are labeled with a second set of acceptors, which emit light at a second wavelength. In this embodiment, the time dependence I(t) is measured for the fluorescence at the first wavelength of the labeled end units and provides information on the velocity of the molecule. The rate is then used to calculate the distance between the labeled interval units based on the time dependence I(t) measured from the fluorescence at the second wavelength.

In yet another embodiment, a mixture of two samples is run simultaneously. In the first sample, the DNA is labeled at the ends with one set of labels that emit light at a first wavelength. In the second sample, the same DNA molecule is labeled at two or more internal units with a second set of labels that emit light at a second wavelength. This experimental arrangement provides substantially the same set of signals described above.

The velocities of all extended objects being measured and used to calculate a particular autocorrelation function are preferably approximately the same. The distribution of velocities affects the sensitivity, accuracy, and resolution of the results determined by the method of the present invention. A more narrow distribution of velocities results in a more narrow peak in $G(\tau)$ at $\tau=<\Delta T>$. Provided that the same proportion of correlated events is detected, the integrated area of the peak should be the same for wider and narrower peaks. Therefore, a sharper peak in the autocorrelation function corresponding to a narrower velocity distribution ensures a better signal/noise (S/N) ratio, i.e., the signal is more discernable above the background noise. The widths of peaks in the autocorrelation function also determine the minimal time intervals between labels on the object that are detectable. Under typical slab electrophoretic conditions, the velocity of short ($\leq 1000$ base pairs) DNA fragments is $10^{-4}$–$10^{-5}$ m/s within the gel matrix, which is used below in further calculations.

An estimate of the velocity distribution within a gel matrix can be obtained from the maximal resolution of the gel separation of DNA fragments according to the following analysis. In electrophoresis of restriction fragments in slab gels, fragments of lengths 300 and 301 can be resolved. Within reasonable approximation, the length differences of DNA fragments is proportional to their velocity differences in gels. The distribution of velocities is not wider than the width of electrophoretic bands of the resolved fragments. Therefore, the width of the velocity distribution inside a polyacrylamide gel matrix is less than 0.3%. This is an overestimate, since other things, such as diffusion of the DNA fragments during the time of electrophoresis, contribute to the widening of bands in a gel. Moreover, the velocities estimated from electrophoresis mobility are actually macroscopically averaged velocities and the distributions are also widened by inhomogeneity of the gel matrix. A more narrow distribution of the microscopic velocities is expected. Indeed, the resolution of fragments of up to 1,000–2,000 bases that differ in length by a single base is achieved in capillary electrophoresis (Sinclair (1999) The Scientist 15 (9): 18–20), which narrows the velocity distribution down to below 0.1%.

As described in greater detail below, any polymer may be analyzed with the methods of the invention. In a preferred embodiment, the objects are rod-like extended molecular complexes. In general, a simple covalent chain-like structure of a polymer is too flexible to ensure rigidity over any significant length. Non-covalent interactions (hydrogen bonds, hydrophobic attraction, dispersion forces, etc.) are needed to form and maintain very extended, stiff, rod like molecular structures. Examples of such structures are plentiful in biology and include, but are not limited to: double stranded DNA, muscle proteins (tropomyosin, myosin), proteins of skin and bones (collagen), viral proteins of the infection system (hemagglutinin of grippe virus), and polyglutamic acid under the conditions promoting formation of long a-helices. The spatial anisotropy of rod-like objects ensures their self-alignment along a flow direction when they are put in motion within liquid media. Indeed, any deviation from this direction results in a pressure component that restores the original alignment due to solvent flow. Thus, the methods of the invention can be performed in virtually any liquid if the extended object has a sufficiently high velocity. The velocity limitation is determined by the following condition: a fluctuation of the label distance from the station should not exceed the characteristic scale, which is dependent on the type of object-dependent impulse analyzed., e.g., the Förster's radius in the case of FRET. While rigidity of an extended object is preferable, it is not an essential property, and the method of the invention may be used with non-rigid objects. The distance constraints can be enforced by using various sample devices (see Section 5.3 below and FIG. 2).

In order to employ FRET in the methods of the invention, both the unit specific marker and the station include fluorophores. In one embodiment, they are single fluorophores. In another embodiment, either the marker, or the station, or both include a plurality of fluorophores. In different embodiments, fluorophores can be fluorescent organic dyes, ions of lanthanide elements, or nanocrystals (or nanoparticles, or quantum dots).

Numerous organic dyes are known in the art. Many of them are available with special reactive groups to form the conjugates of the dyes with different objects (see for example Haugland (1996) "Handbook of Fluorescent Probes and Research Chemicals", Molecular Probes, Inc.). The conjugates can be formed through covalent and non-covalent linkage. Examples of organic fluorescent dyes that can be used to label extended objects or stations include xanthene dyes, BODIPY™ dyes, coumarin dyes, rhodamine dyes, and fluorescein dyes. Other fluorescent compounds are well-known to those skilled in the art and can be found, e.g., in Haugland (1996) *Handbook of Fluorescent Probes and Research Chemicals, Sixth Edition,* (Molecular Probes, Inc.).

Lanthanide ions provide several advantages for FRET measurement. First, the energy transfer distance is larger than for most organic dye pairs ($Z_F$=7 nm for lanthanides in $D_2O$ in contrast to $Z_F$=2–5 nm for organic dye molecules). Second, the excited states of lanthanides have long lifetimes (0.1–1 ms), which allows for ease of measurement in time-gated fluorescence experiments. One disadvantage of lanthanides is that their fluorescence is quenched in water by radiationless energy transfer between the excited lanthanide ion and the water molecules in the coordination sphere. In order to overcome this problem, lanthanides for fluorescent applications are coordinated to bulky, hydrophobic ligands in order to isolate them from direct contact with water (Saha et al. (1993) J. Amer. Chem. Soc. 115:11032–11033). A second disadvantage of using lanthanides as fluorophores is their relatively low extinction coefficient. In order overcome this problem and increase the absorption cross-section of lanthanide ions, they are coordinated to ligands that have strong absorption (Selvin & Hearst (1994) Proc. Natl. Acad. Sci. U.S.A. 91:10024–10028; Selvin et al. (1994) J. Am. Chem. Soc. 116:6029–6030).

Nanocrystals are tiny pieces of inorganic semiconductor crystals (e.g., CdSe or InAs) with sizes ranging from single nanometers up to hundreds of nanometers (Alivisatos (1996) J. Phys. Chem. 100: 13226–13239). Depending upon their size and material, nanocrystals emit in different regions of the electromagnetic spectrum, even when excited with the same wavelength (Bruchez et al. (1998) Science 281: 2013–2016). Special coating procedures are applied to stabilize them in solution and make possible their conjugation with different objects (Chan & Nie (1998) Science 281: 2016–2018). The advantage of nanocrystals is their high brightness of emission and high stability against photobleaching. One disadvantage of the nanocrystals is their relatively large size in comparison with organic dyes and chelated ions, which decreases resolution. Another disadvantage of nanocrystals is that the stabilizing coating increases the donor-acceptor separation, which may decrease FRET efficiency.

Donor-acceptor fluorophore pairs are preferably chosen such that the emission spectrum of the donor overlaps with the excitation spectrum of the acceptor (Selvin (1995) Meth. Enzymol. 246: 300–334; Wu & Brand (1994) Anal. Biochem. 218: 1–13). Examples of such preferred donor-acceptor fluorescent dye pairs include, but are not limited to: fluorescein and Texas Red®; Oregon Green™ and Texas Red®; fluorescein (or Oregon Green™) and x-rhodamine; and tetramethylrhodamine and Texas Red®. More preferably, the donor-acceptor dye pairs include, but are not limited to: Alexa™ 488 and Texas Red®; Alexa™ 488 and x-rhodamine; tetramethylrhodamine and Cy5; terbium (Tb$^{3+}$) ion and tetramethylrhodamine (TMR); or europium (Eu$^{3+}$) ion and Cy5.

In some embodiments, the present invention involves the labeling of proteins. For example, protein channels or molecular motors can be used in devices at stations in order to guide extended objects past a station. Furthermore, an extended object for analysis by the methods of the present invention may be comprised of amino acids. In order to make fluorescent labeling of proteins possible, amino acids with reactive side chains can be introduced at strategic points by means of, e.g., protein engineering (Buckle et al. (1996) Biochemistry 35: 4298–4305; de Prat-Gay, (1996) Protein Engineering 9: 843–847). These reactive side chains can be further fluorescently labeled by techniques known in the art (see, for example, Haugland, "Handbook of Fluorescent Probes and Research Chemicals" (1996) Chapters 1–3, 7, 15, 18).

Most preferably, the extended object for analysis using the methods of the present invention is DNA. Unit-specific markers may be incorporated into the DNA molecule to be analyzed in many ways. In one embodiment, fluorescent nucleotide analogs can be introduced into a polynucleotide during synthesis (Jameson & Eccleston (1997) Meth. Enzymol. 278: 363–390). In another embodiment, fluorescent dyes can be attached via reactive groups on the DNA and the dye (Langer et al. (1981) Proc. Natl. Acad. Sci. U.S.A. 78: 6633–6637; Waggoner (1995) Meth. Enzymol. 246: 362–373). In yet another embodiment, lanthanide ions can be attached to DNA via chelating groups (Selvin & Hearst (1994) Proc. Natl. Acad. Sci. U.S.A. 91: 10024–10028; Selvin et al. (1994) J. Amer. Chem. Soc. 116: 6029–6030; Kwiatkowski et al. (1994) Nucl. Acids Res. 22: 2604–2611; U.S. Pat. No. 5,591,578). Fluorophores can be attached to the ends of a DNA fragment or to particular reactive groups on the nucleobases. They may be attached to DNA via natural or artificially introduced reactive groups, either prior to or after DNA synthesis.

Unit-specific markers may also be short oligonucleotide probes that are complementary to a sequence within the DNA molecule to be analyzed. Labeled oligonucleotide probes can be made using any of the techniques described above. Preferably, the oligonucleotide probe is labeled with any relatively small fluorophore at either the 3' or 5' end. In a preferred embodiment, oligonucleotide probes hybridize to target nucleic acids to form duplexes, triplexes or higher order structures and the label is introduced by virtue of the hybridization. Sequence specific hybridization can be performed by art recognized methods (Young and Anderson (1985) in "Nucleic Acid Hybridisation: A Practical Approach", 47–71). An oligonucleotide probe comprised of 15–20 nucleotides will bind specifically to a complementary sequence without random, non-specific binding.

Most preferably, the probes are peptide nucleic acids (PNA), in which the phosphate sugar backbone of nucleic acids is replaced by a peptide-like backbone based on the monomer 2-aminoethyleneglycin having any sequence of nucleobases. This polymer, in contrast to RNA or DNA, is electrically neutral. A PNA probe can be charged by adding, e.g., a fluorescent label, lysine or other positively charged amino acid residues at one of the termini. An RNA or DNA hybrid with a PNA is more stable than a complex of nucleic acid hybridized with another nucleic acid. Below the melting point, a PNA antisense sequence of ~20 nucleotides binds to its target RNA or DNA within a suitable equilibration time and remains bound to the target sequence for days, even if excess unbound primer is removed.

Both protein and nucleic acid labeling procedures can be used to label a PNA. Furthermore, PNA chimeras with special polypeptide sequences can acquire extra functions. For example, a (His)$_6$-PNA chimera exhibits strong binding to chelated Ni$^{2+}$ ions without compromising its native PNA hybridization properties (Orum et al., (1995) BioTechniques 19: 472–480). Potentially, this chelating functionality could be used to label the PNA with a lanthanide ion fluorophore.

Oligonucleotide or PNA probes can be used in the methods of the present invention for the analysis of DNA sequence. If a labeled probe binds to a DNA analyzed by the methods of the present invention at a specific site, then the location of the site and its sequence are known. If the DNA molecule itself is not labeled, then only DNA molecules to which at least two labeled probes are bound will give rise to a corresponding maximum in the autocorrelation function. The same DNA fragment can be further analyzed with different probes and the complete sequence of the DNA fragment can be elucidated. This approach is similar to sequencing by hybridization, in which a target nucleic acid sequence is determined using data about its hybridization with a specific set of oligonucleotides (Strezoska et al. (1991) Proc. Natl. Acad. Sci. U.S.A. 88: 10089–10093; Bains (1992) BioTechnology 10: 757–758). However, there is a major difference between this method and methods of the present invention. In "classical" sequencing by hybridization, the binding of probes to the target DNA is first determined. When all probes capable of binding to the DNA are identified, the whole DNA sequence is restored by alignment of the probe sequences, which is done using overlapping fragments of the probes. This is a laborious procedure requiring enormous computer resources (Bains (1992) BioTechnology 10:757–758). This limits maximal length of the target DNA that can be sequenced to relatively short fragments below 1000 bases. In the methods of the present invention, not only is information about hybridization of test probes to a target DNA available, but also the distance between the probes on the target DNA.

The approach to sequencing is illustrated in FIG. 3A. In a first run, the hybridization of the probes a and b are detected and the distance between them is determined. In a second run, the hybridization of the probes g and d are detected and the distance between them is determined. If a and g are overlapping probes, the relative positions of all four complementary sequences a–d are determined in the target DNA. In one embodiment, only one test probe is used and the second fluorophore is attached to the terminus of the target DNA (FIG. 3B). In this case, the position of the tested sequence is determined relative to the labeled end of the target DNA molecule.

For short oligonucleotides, there is a possibility that it will hybridize to more than one complementary site on the target DNA. One way to decrease the probability of multiple binding sites for a single probe is to use longer probes. Conversely, if the number of complementary sites on the target DNA is small and all peaks in the autocorrelation function are resolved, then multiple probe binding sites do not cause a problem. In this case, all separation distances between the probe binding sites can be determined. The peaks in the autocorrelation function correspond to the interlabel intervals and their combinations. If for instance, three probes a, b, and g are bound to the target, the peaks corresponding to the distances $L_{ab}$, $L_{bg}$, $L_{ag}$, $(L_{ab}+L_{bg})$, $(L_{ab}+L_{ag})$, and $(L_{bg}+L_{ag})$ would occur in the autocorrelation function.

Multiple probe binding can be used for identification properties. In this case, shorter probes or a "cocktail" of different probes (see U.S. Pat. No. 5,807,677) can be used. The composition is chosen to ensure multiple binding. The autocorrelation function will exhibit a complex pattern of peaks whose positions and intensities depend upon the number of bound copies of each oligonucleotide and the distances between them. To enhance identification ability, different oligonucleotides may be labeled with different fluorophores and several autocorrelation functions, each of them measured in the corresponding spectral range, can be used together. It may not be necessary to determine the exact binding patterns. Rather, the complex pattern of labels can be used as a "fingerprint", which may be useful in, e.g., forensic analysis.

An advantage of this embodiment of the invention is that the same DNA sample can be used for multiple characterizations. After a run with one set of oligonucleotide probes, they can be removed from the DNA by techniques known in the art, e.g., denaturation of the DNA sample under appropriate conditions (see, e.g., Young and Anderson (1985) in "Nucleic Acid Hybridisation: A Practical Approach", 47–71). The dissociated probes are removed, e.g., by electrophoresis in the direction perpendicular to that of target DNA movement during analysis, and the DNA is subsequently coupled with another set of probes and is re-run on the same network of stations, e.g., by reversing the direction of movement. The methods of the invention are amenable to this type of analysis for two reasons. First, there is no need to concentrate the DNA to form the band; rather a signal volume of any size can be analyzed and is limited only by background intensity. Second, the method is insensitive to unbound probe, since only oligomers bound to the same object can produce a correlated signal.

It is also possible to reanneal the same set of probes to the target DNA and reanalyze it. Thus, the same DNA sample can be relabeled in order to remove photobleached fluorophores. This restored sample can also be run in another region of the matrix where the stations have not yet been used and therefore are not photobleached. The opportunity for multiple use of the same sample in the methods of the invention either to enhance statistics or for complementary analyses allows the use of small amounts of sample (potentially down to the single molecule level) for elaborate analyses.

The methods of the invention can also be used for multiplex detection of individual gene targets and determination of how far they are separated on the same DNA molecule. Both single- and multiple-probe approaches are possible. When applied to several different target nucleic acids, the methods of the invention permit the detection of multiple gene targets in the same test sample. In one embodiment, degenerate or partially degenerate probes can be used. This multiplex detection allows determination of the degree of genetic identity in genetically uncharacterized organisms. In another embodiment, degenerate probes can be designed to hybridize to the 3' and 5' ends of repeated sequences so as to detect an undetermined number of the repeated sequence, many copies of which are dispersed throughout the genome. A complex pattern in the autocorrelation function results from the analysis and may serve as a "fingerprint" of the studied DNA. The same fluorophore can be used to label different oligonucleotide probes, and the fingerprint is the distribution of distances between recognized sites. In a preferred embodiment, several sets of oligonucleotide probes labeled with different fluorophores are used.

The methods of the invention can also be used to determine if two fragments have been joined during a ligation reaction. For this, two oligonucleotide probes, each specific for a sequence on one of two fragments to be ligated, are used. The same fluorophore is used to label both oligonucleotide probes. When ligation of the fragments bound to the probes occurs, a peak appears in the autocorrelation function, since the probes are now labeling one extended object.

5.3 Apparatus for Correlated Fred Analysis

FIG. 4 depicts a schematic diagram of an optical setup for the measurement of correlated FRET. A laser is used as an excitation light source, LS. Various ion lasers can be used, including but not limited to argon lasers (major lines at 488, 514.5, 351.1, and 363.8 nm), krypton lasers (major lines at 568.2, 647.1, and 752.5 nm), copper lasers (major lines at 510 and 578 nm), helium-neon lasers (major lines at 543.5, 594.1, 611.9, and 632.8 nm), and helium-cadmium lasers (major lines at 325 and 441.6 nm). In different embodiments, either one of the major lines or (in some cases) a combination of the neighboring lines can be used. In other embodiments, crystal and diode lasers can used in their multiple modes, which include but are not limited to nitride blue diode lasers such as InGaN or AlGaInN (emission between 390 and 425 nm), Nd:YAG lasers (266(4×), 354.7 (3×), 532(2×), and 1064 nm), Ti:sapphire lasers (330–600 (2×) and 660–1200 nm), and alexandrite lasers (360–400 (2×) and 720–800 nm). In another embodiment, pulsed lasers with high repetition rates ($\geq$10 kHz are preferred, $\geq$1 MHz are most preferred) are used. In yet another embodiment, powerful arc lamps, e.g., high-pressure xenon, mercury, or mercury/xenon, are used. Most preferably, a continuous wave (CW) laser is used as the excitation light source.

The excitation light, e.g, laser beam, passes through attenuator AT and line filter LF to modulate the light intensity and select a proper excitation line, respectively. After passing through the beam expander E, the excitation light is reflected from dichroic mirror DM toward the sample mounting. The dichroic mirror reflects light of the excitation wavelength and transmits light of the acceptor emission wavelength. The excitation light is focused on the sample S by means of the sample lens SL. In one embodiment, the sample lens is an aspheric lens. In another embodiment, it is a microscope objective. The sample comprises an assembly of labeled extended objects moving through a network of D-centers (see Section 5.3 for the articles of manufacture that arrange samples for correlated FRET analysis). As sample emission occurs in the focus of the sample lens SL, it is collected by the sample lens and exits it on the opposite side as a parallel beam. The emission light is directed through the dichroic mirror, bandpass filter BF, and collecting detector lens DL. The detector lens focuses the emitted light on the pinhole P that performs as a spatial filter (confocal optics arrangement), cutting out a large portion of background photons. The filtered emitted light is directed to a photodetector PD. Those who are experienced in the art can appreciate introduction of a notch-filter (to cut the excitation light) and shutters in front of the light source and/or photodetector for further filtering (neither notch-filter nor shutters are shown in FIG. 4).

Simple optical elements like attenuator, beam expander, pinholes, simple lenses, sample compartment and other light protected components are available from many manufacturers (Newport, Oriel Instruments, Rolyn Optics, Thorlabs Inc., to enumerate few). Optical filters and dichroic mirrors for various spectral ranges can be ordered from Chroma Technology Corp, Omega Optical Inc., and Kaiser Optical Systems Inc. Microscope objectives can be ordered from Carl Zeiss, Inc. or from Nikon, Inc. It is important to use components with minimal background fluorescence. All lenses, filters, attenuators and mirrors are manufactured from fused silica (quartz) in the preferred embodiment. In a preferred embodiment, low-fluorescent, infinity corrected, specialized microscope objectives, such as Plan-NEOFLUOAR 40×/NA 1.30 (oil immersion) or FLUAR 40×/NA 1.30 (oil immersion), from Carl Zeiss, Inc. can be used. For deep blue and ultraviolet excitation light, a UV-transparent microscope objective with water immersion, such as C-APOCHROMAT 40×/NA 1.2, is preferred.

The pinhole diameter depends upon the parameters of the other optical components used. In one embodiment (FIG. 4), the laser beam diameter is 0.7 mm, a 3× beam expander is used, the sample lens is aspheric with an effective focal length of 14.5 mm, and the detector lens is plano-convex with a focal length of 100 mm. In this configuration, the diameter of the illuminated active spot on the sample is £0.05 mm. Hence, the diameter of the pinhole should be $^3$0.35 mm. In another embodiment, the Plan-NEOFLUOAR 40× microscope objective is used instead of an aspheric lens. In this case, the size of the illuminated spot on the sample is 1.2 $\mu$m. Hence, the diameter of the pinhole should exceed 30 $\mu$m. In a preferred embodiment, pinholes are used that have diameters that are about 1.5 times larger than the diameter of the image of the illuminated active spot on the sample to provide an optimal combination of restriction of background and intense sample emission. In this case, pinholes with diameters of 0.53 and 0.045 mm should be used with the aspberic lens and microscope objective, respectively. Either the aspheric lens or the microscope objective should be used as the sample lens to provide maximal collection efficiency of sample emissions.

The photodetector used in the optical setup should be sensitive enough to detect single photons, it should have high quantum efficiency in the spectral region where the acceptor fluorophore emits and low background noise. In a preferred embodiment, a photomultiplier tube (PMT) is used. In a more preferred embodiment, the PMT should have an AsGa photocathode for high quantum efficiency in a wide spectral range. For example, PMT R943-02 (Hamamatsu) has a quantum efficiency greater than 15% at wavelengths of less than or equal to 570 nm and a quantum efficiency greater than 10% at wavelengths of less than or equal to 840 nm. A typical PMT of this type has dark current of less than 5 cps (counts per second) with its photocathode cooled below −30° C. To process the signal output, the PMT in photon counting mode is better used with a wide band preamplifier (e.g., SR445 of Stanford Research Systems) and discriminator. The discriminator is often included in the input circuitry of some multichannel analyzers (SR430 of Stanford Research Systems) or may by purchased separately (Canberra's Model 2126).

In another embodiment, the detector is an avalanche photo diode (APD). This device is available as part of an integrated single photon counting module (SPCM-AQR-15-FC, EG&G Optoelectronics), which includes an APD cooler as well as all electronic circuitry needed for signal conditioning. A typical SPCM module has a quantum efficiency of greater than 80% at 600–700 nm and a dark current below 50 cps.

In yet another embodiment, the detector is a multichannel plate PMT (MCP-PMT). This device is related to the PMT and has similar parameters, except for the intrinsic time. While typical intrinsic times of PMTs are within the range of 1–10 ns, the intrinsic times of MCP-PMTs can be as low as 0.1 ns. More preferably, a gateable MCP-PMT (like R2024U, Hamamatsu) is the detector.

In one embodiment, the signal is monitored using CW laser sample excitation and continuous detection of the emission signal. In another embodiment, a pulse laser can be used for sample excitation. In this embodiment, detection of emission signal is laser pulse-coupled and the preferred detection mode is the time-correlated single photon counting ("TCSPC") mode, which further reduces background due to scattering (Shera et al. (1990) Chem Phys. Lett. 174: 553–557). The laser pulse rate depends upon, inter alia, the laser intensity, the lifetime of the fluorophores, and photobleaching effects. A typical pulse rate is between 10 and 80 MHz. A gateable MCP-PMT detector is used and is gated between the pulses to detect fluorescence emission, which generally has a longer half-time than the Rayleigh and Raman scattering that contribute to background. In a preferred embodiment, FRET is used to detect the object-dependent impulse, which eliminates the need for time-gated detection because the emission region is far separated from the excitation wavelength and generally does not include solvent scattering.

An autocorrelation function for data processing can be obtained either during data collection by using specialized hardware, or by post-collection computer processing of the data. In one embodiment, an autocorrelation function can be calculated using the Professional version of the LabVIEW software package (National Instruments). In another embodiment, the methods disclosed in U.S. Pat. No. 5,404,320 can be implemented in either the software or the hardware in order to obtain an autocorrelation function. In the embodiment depicted in FIG. 4, the time dependence of the emission is collected in a multichannel analyzer MA (SR430, Stanford Research Systems) during the measurements, is transferred to computer C and is processed with a routine for the calculation of an autocorrelation function.

The invention also relates to computer system for analyzing an extended object labeled with at least two unit-specific markers comprising: a central processing unit; an input device for inputting a plurality of object-dependent impulses of an extended object; and output device; a memory; at least one bus connecting the central processing unit, the memory, the input device and the output device, the memory storing a calculating module configured to calculate an autocorrelation function for said plurality of object-dependent impulses of said extended object input using said input device.

The invention further relates to a computer program product for use in conjunction with a computer, the computer program product comprising a computer readable storage medium and a computer program mechanism embedded therein, the computer program mechanism comprising a calculating module configured to calculate an autocorrelation function of a plurality of object-dependent impulses.

The data generated using the autocorrelation function provides information about the extended object. In a preferred embodiment, a set of identical objects having identical labels is examined. The data produced by these objects and interpreted using an autocorrelation function reveal the identity of patterns of unit-specific markers on the extended objects.

5.4 Sample Devices for Correlated Fret Analysis

Optimization of FRET is dependent upon the spatial proximity of the interacting fluorophores during the energy transfer. According to formula 1, the fluorescence transfer efficiency is inversely proportional to the sixth power of Z, the distance between donor and acceptor molecules. The distance at which FRET occurs with 50% probability (the Förster's radius $Z_F$) is between 2 and 7 nm for most pairs of fluorophores (Wu & Brand (1994) Anal. Biochem. 218: 1–13). Therefore, in order for optimal FRET interaction between the molecules of the dye pair to occur, the label (either D or A) on the polymer must pass within 2–7 nm of its partner (either A or D) at the station. Those with skill in the art will recognize that, when donor molecules are on the extended objects, acceptor molecules will be at the stations, and alternatively, when acceptor molecules are on the extended objects, donor molecules will be at the interaction stations. Therefore, although the embodiments may be described with donors at the stations and acceptors on the extended object, it will be understood that these embodiments also encompass experimental set ups with acceptors at the stations and donors on the extended object.

Described in this section and shown in FIGS. 5A–5C are articles of manufacture for correlated FRET analysis of extended objects. Although all discussions here involve articles of manufacture for correlated FRET analysis, it will be understood by those with skill in the art that similar configurations with minor changes, e.g., station types or dimensions, can be used for monitoring other physical effects that are object-dependent impulses.

Several possible devices for accomplishing correlated FRET methods are set forth in more detail below. For example, a lattice with scattered D-centers, channels with D-centers at their periphery, or a molecular motor comprising a D-center or in the vicinity of a D-center can be used to accomplish the methods of the invention. Any device that will promote the linear passage of all acceptors bound to a single extended object past the same D-center in order to produce object-dependent impulses is contemplated by the invention. When more than one D-center is analyzed according to the methods of the invention, the plurality of D-centers should be distributed so that there is no interference of the signals. The distribution of the D-centers is adjusted so that the time interval $\Delta T$ between the events arising as a result of different acceptors on the same object passing in interactive proximity with the one D-center is shorter than the time interval between the events arising as a result of one acceptor passing in interactive proximity to different D-centers.

In one embodiment, the extended objects move through the gel that includes D-center stations bound covalently to the gel network (FIG. 5A). In this case, the function of the gel matrix is to organize and support a spatially distinct network of stations. This approach is feasible only if the tangential displacement (in the direction perpendicular to motion) of the extended objects during DT, the time interval between subsequent passes of acceptors attached to a single extended object past the same D-center, is small enough not to change the optimal FRET distance dramatically. Although longitudinal movement of the extended object is forced, the tangential displacement fluctuates, and hence, decreases with decreased DT. The interval DT can be decreased by increasing the longitudinal speed ol the extended object, e.g., by increasing the voltage of the electric field used as the driving force. Increased longitudinal speed will also increase solvent resistance to movement of the extended object, which in turn favors a small molecular cross-section in the longitudinal direction and therefore helps to eliminate tangential movement of the extended object. Increased solvent resistance can also be accomplished by changing, inter alia, the solvent viscosity, temperature, gel concentration.

The same system with a higher concentration gel can be used to analyze longer and more flexible extended objects. Denser gel networks not only support the network of spatially distinct stations, but also direct the movement of the extended object so that the entire object follows the same pathway past stations through the gel. In this case, the speed of the extended object V is used to maintain the spatial separation $L_i$ of the labels on the extended object that corresponds to time interval $t_i$ determined from the autocorrelation function. In order to determine the value of V, different acceptors $A_2$ are placed on an extended object at sites separated by a known distance. The dependence I(t) is measured in the spectral range of these $A_2$ acceptors and can be used to determine the proper value of V for the configuration.

Most preferably, the gel material is polyacrylamide. Efficient mobility of DNA fragments of up to 12,000 base pairs in length in non-denaturing conditions was reported (Heiger et al. (1990) J. Chromatogr. 516: 33–48) within polyacrylamide matrices. An example of introduction of fluorophores into a gel network is presented below in Example 1.

The resolution of FRET analysis is now calculated for a device comprising a low concentration gel with stations and for examination of relatively rigid extended objects. For a particular configuration, the potential resolution of FRET analysis is determined by the distances between acceptors and donors within which FRET can occur (FIG. 6). For each trajectory of an acceptor, there is the shortest distance to the nearest donor center that corresponds to the maximal efficiency of FRET. Before and after the acceptor reaches this position, the energy transfer is less efficient. For the following calculation, the boundary of the FRET region is where the efficiency of energy transfer is ⅕ of the maximal efficiency. Energy transfer to the acceptor beyond this FRET region is neglected. The size of the FRET region dL determines the geometric resolution of the method because the energy transfers within the FRET region are indistinguishable from one another.

The effective size of the D-center $\delta L_D$ is the sum of the geometric size of a donor molecule and of the amplitude of its displacement relative to the acceptor. The displacement is considerable when both D and A groups are attached via flexible linkages. In the typical case, $dL_D$ is 1–5 nm. For the purpose of this calculation, the shortest separation between the moving acceptor and the D-center is $Z_0=5$ nm (a typical Förster radius $Z_F$ value). The border of the FRET region $\delta L$ is where the distance $(Z_0+\Delta Z)$ separates the acceptor and D-center. The value of $\Delta Z$ is determined from the condition that FRET is 5 times less efficient at $(Z_0+\Delta Z)$ than at $Z_0$. Assuming a dipole-dipole interaction mechanism, the efficiency ratio is $((Z_0+\Delta Z)/Z_0)^6=5$, which gives $\Delta Z=0.308Z_0$. The distance $\delta L_Z$ between the acceptor positions with the separations of $Z_0$ and $(Z_0+\Delta Z)$ from the D-center is $\sqrt{((Z_0+\Delta Z)^2-Z_0^2)} >> \sqrt{(2Z_0\Delta Z)}=0.784Z_0$. The overall size of the FRET region $\delta L=\delta L_D+2\delta L_Z=9-13$ nm. These estimations are done for acceptor displacement along the direction of the extended object movement. If the tangential displacement of acceptors is large relative to $Z_F$, the efficient value of $\delta L_Z$ will be diminished. Such displacement decreases the proportion of correlated FRET events.

In another embodiment, a spatial network of stations is organized using a matrix of beads (FIG. 5B). When densely packed, the beads form channels of defined sizes due to hexagonal close packing. The movement of the extended object through channels between the beads is similar to the movement of a molecule through a densely packed column matrix, with the exception that the diameter of the beads used in this embodiment of the present invention is much smaller than the diameter of beads used in conventional separation techniques, e.g., high performance liquid chromatography columns. Preparations of highly ordered lattices of beads with diameters between 180 and 1500 nm are known in the art (Holland et al. (1998) Science 281: 538–540; Wijnhoven & Vos (1998) Science 281: 802–804).

The size of the channels between the beads, and therefore the distance between stations on the beads and unit-specific markers on the extended objects traveling through the channels, is adjusted by choosing beads of a given diameter. For example, given beads that are ideal spheres of 65 nm diameter that pack into an ideal hexagonal lattice, any point of the extended object travelling through a channel in this lattice will always be located within 5 nm of the surface of the nearest bead. Polystyrene beads with diameters as small as 20 nm are commercially available.

The stations within the lattice can comprise anything that will produce label-dependent impulses when the labeled extended object passes within interactive proximity of the station. Preferably, the stations in the lattice comprise fluorescent units. In a preferred embodiment, the lattice comprises fluorescent beads or beads labeled with fluorescent donors or acceptors. The small size of the beads and the fact that their refractive index matches that of the solvent decrease light scattering, and are therefore advantageous for light penetration into the matrix. As a result, the excitation radiation can penetrate at least several microns into the packed bead matrix. The movement of the extended object through the bead lattice exactly resembles the movement of the extended object through a dense gel network. An estimation of the resolution of FRET analysis using a bead lattice is calculated in Example 1 below.

Polystyrene beads having a variety of diameters from 20 nm to 1 mm are commercially available (Bangs Laboratories, Inc., Fishers, Ind.; Molecular Probes, Inc., Eugene, Oreg.). The beads may already have fluorophores incorporated into them (e.g., FluoSpheres of Molecular Probes, Inc.) or covalently conjugated to their surface (Bangs Laboratories, Inc.). Alternatively, beads with surface reactive groups (e.g., amino groups) can be ordered or prepared according to the techniques known in the art, and labeling can be performed using numerous commercially available reactive dyes. Labeling of polystyrene beads can be done by swelling the beads in a solution of organic solvent (the proper solvent or solvent mixture is determined according to solubility tables and the molecular weight of the polystyrene) and a water-insoluble dye. In one embodiment, a bead has only one fluorophore attached. In another embodiment, a bead is densely labeled and can be treated as a single fluorescent center of the size of the bead. In a preferred embodiment, each bead includes more than one fluorescent center.

The design of the container wherein the beads are packed depends upon the monitoring optics system and the force chosen to move the extended objects through the beads. For example, if pressure is used to move the extended objects, the container must be designed to withstand increased pressure. The container must be transparent in the excitation and emission spectral regions.

An estimation of the FRET region dL (see above in this section) for the lattice of beads is illustrated in FIG. 7. Within the lattice of beads with a diameter of 65 nm=2R, the moving DNA fragment is never more than $Z_0$=5 nm from the nearest bead surface. A portion of fluorescently labeled beads is embedded into the lattice, which serve as D-centers.

In this case, the distance to the D-center is the distance to the surface of a fluorescent bead in the lattice and $\delta L=2\sqrt{((R+Z_0+\Delta Z)^2-(R+Z_0)^2)}>>\sqrt{(2(R+Z_0)\Delta Z)}=22$ nm.

In yet another embodiment, extended objects can be threaded through narrow channels in a membrane, wherein one surface of the membrane is covered with stations (FIG. 5C). Current technology allows the production of channels with diameters as small as 10 nm. The D-centers that form the stations can be attached to one of the membrane surfaces by, inter alia, covalent bonding (in a molecular monolayer), by the Langmuir-Blodgett technique (molecular mono- or multi-layer), by spin coating (down to 10 nm), etc. All fluorescence of the bound acceptors is localized in vicinity of the membrane surface in this configuration. A representative protocol for preparation of nanochannels and estimation of the FRET resolution using this embodiment of the present invention is enumerated in Example 1, below. DNA fragments having as many as 48,000 base pairs were efficiently moved by electrophoresis through 10 nm channels without noticeable destruction. Our study of DNA transport through the PCTE membrane showed that DNA molecules can be efficiently transported through the long (5 μm) channels with diameter as small as 10 nm. Even DNA fragments as long as lambda phage DNA (48,000 base pairs long) can be transferred through these channels without considerable fragmentation.

For the configuration of a membrane with channels, the estimation of FRET resolution is essentially the same as for the configuration with the gel-bound donors (see above in this section). If the DNA fragment (diameter=2 nm) is centered within a channel of diameter 10 nm, the separation $Z_0$ between the moving acceptor and the D-center (the layer with donor fluorophores) is 5 nm. The size of the D-center $dL_D$ is actually the thickness of the layer (1 and 10 nm for molecular monolayer and spin-coating fluorescent layer depositions, respectively). The prediction gives $\delta L=\delta L_D+2\delta L_Z=9-18$ nm.

PCT Publication No. WO 98/35012, which is incorporated herein by reference in its entirety, provides a detailed description of various articles of manufacture comprising embedded fluorophores that are useful for practicing the methods of the present invention.

5.5 Structures for Stretching Polymers

Most biological polymers do not exist in solution in their fully extended conformations. Rather, intra-molecular interactions cause them to exist in more condensed, coiled conformations in solution. For example, a DNA molecule in solution exists in a coiled conformation with a diameter of 10 μm. Without being bound by any theory, it is substantially more difficult to analyze polymers in condensed conformations than in their fully extended forms. Therefore, it is preferable to extend polymers for analysis in the devices described above in Section 5.4.

Structures that allow polymers of any length, including nucleic acids containing entire genomes, to be stretched into a long, linear conformation for further analysis may be used in conjunction with the methods and apparatuses of the present invention (see U.S. patent application Ser. No. 60/149,020 entitled "Methods And Apparatuses For Stretching Polymers," inventors Rudolf Gilmanshin and Eugene Chan, filed on even date herewith and incorporated herein by reference in its entirety). Polymers are loaded into a device and run through the structures, propelled by, inter alia, physical, electrical or chemical forces. Stretching is achieved by, e.g., applying shear forces as the polymer passes through the structures, having the polymer trace out a torturous path, placing obstacles in the path of the polymer, or combinations thereof. Because the forces are applied continuously, it is possible to stretch out polymers to a length that is equal to or greater than the active area of the apparatus, i.e., where information about the polymer is collected as the polymer is analyzed. Since multiple molecules may be stretched in succession, extremely high throughput screening, e.g., screening of more than one molecule per second, is achieved.

The structures comprise two components: a delivery region and a region of polymer elongation. The delivery region is a wider channel that leads into and out of the region of polymer elongation. The region of elongation comprises at least one of four main components: (1) funnels; (2) structures having branched channels; (3) channels with bends or curves; and (4) obstacles defining small gaps. The structures may comprise combinations of the four main components and variations of the main components themselves. A combination of two or more of the main component features can give rise to additional designs that work well to extend and stretch polymers, particularly DNA, in a controllable fashion. In addition, several of the same design may be repeated in parallel or in series.

Examples of structures (FIG. 8) that can be used in conjunction with the methods and apparatuses of the present invention include, but are not limited to:

i) funnels with a non-linear increase in fluid velocity;
ii) funnels with a linear increase in fluid velocity;
iii) funnels with obstacles defining small gaps as the region of DNA elongation;
iv) funnels with a non-linear increase in flow rate and obstacles defining small gaps;
v) funnels with a linear increase in flow rate and obstacles defining small gaps;
vi) funnels with mixed obstacle sizes and gaps, including a gradient of obstacles sizes and gaps;
vii) branched structures having regions of increased flow rates from converging channels;
viii) branched structures having multiple regions of increased flow rates from multiple converging channels;
ix) branched structures having obstacles defining small gaps;
x) branched structures which have at least one funnel as one of the branches;
xi) branched structures with mixed obstacle sizes and gaps, including a gradient of obstacle sizes and gaps;
xii) structures which have obstacles which define small gaps and also bends or curves;
xiii) structures which have obstacles defining small gaps which have a periodicity (sine patterns, boxcar repeats, zig-zags);
xiv) structures which have obstacles defining small gaps which are non-quadrilateral polygons;
xv) structures having a mixture of obstacles which define small gaps, e.g., a set of bars defining small gaps juxtaposed to a field of sine patterns, or a field of triangles, circles, or stars;
xvi) structures having obstacles defining small gaps integrated with funnels, branched structures, or bends or curves;
xvii) structures having bends or curves in a funnel shape;
xviii) structures having bends or curves with obstacles defining small gaps;
xix) structures having regions of DNA elongation in series;
xx) structures having regions of DNA elongation in parallel;
xxi) structures having multiple delivery channels with respective regions of elongation; and
xxii) structures having three-dimensional geometries involving embodiments of the other categories; and
xxiii) Structures which are closed loops containing regions of DNA stretching.

The most preferred embodiment is a structure that combines posts with two regions of differing funnel designs, as shown in FIG. 9. Pressure flow is the preferred driving force because of the predictable behavior of fluid bulk flow.

Structures are constructed on a substrate selected for compatibility with both the solutions and the conditions to be used in analysis, including but not limited to extremes of salt concentrations, acid or base concentration, temperature, electric fields, and transparence to wavelengths used for optical excitation or emission. The substrate material may include those associated with the semiconductor industry, such as fused silica, quartz, silicon, or gallium arsenide, or inert polymers such as polymethylmetacrylate, polydimethylsiloxane, polytetrafluoroethylene, polycarbonate, or polyvinylchloride. Because of its transmissive properties across a wide range of wavelengths, quartz is a preferred embodiment.

The use of quartz as a substrate with an aqueous solution means that the surface in contact with the solution has a positive charge. When working with charged molecules, especially under electrophoresis, it is desirable to have a neutral surface. In one embodiment, a coating is applied to the surface to eliminate the interactions which lead to the charge. The coating may be obtained commercially (capillary coatings by Supelco, Bellafonte Pa.), or it can be applied by the use of a silane with a functional group on one end. The silane end will bond effectively irreversibly with the glass, and the functional group can react further to make the desired coating. For DNA, a silane with polyethyleneoxide effectively prevents interaction between the polymer and the walls without further reaction, and a silane with an acrylamide group can participate in a polymerization reaction to create a polyacrylamide coating which not only does not interact with DNA, but also inhibits electro-osmotic flow during electrophoresis.

The channels may be constructed on the substrate by any number of techniques, many derived from the semiconductor industry, depending on the substrated selected. These techniques include, but are not limited to, photolithography, reactive ion etching, wet chemical etching, electron beam writing, laser or air ablation, LIGA, and injection molding. A variety of these techniques applied to polymer-handling chips have been discussed in the literature including by Harrison et al. (Analytical Chemistry 1992 (64) 1926–1932), Seiler et al. (Analytical Chemistry 1993 (65) 1481–1488), Woolley et al. (Proceedings of the National Academy of Sciences November 1994 (91) 11348–11352), and Jacobsen et al. (Analytical Chemistry 1995 (67) 2059–2063).

5.6 Methods for Sample Movement

Mechanical (e.g., pump or plunger), electroosmotic, or electrokinetic means may be used in the methods of the invention to move the extended objects past stations in order to generate an object-dependent impulse. In the case of mechanical and electroosmotic forces, the extended object is put into motion by the flow of a stream of solvent. In a preferred embodiment, mechanical or electroosmotic forces are used to move extended objects through a bead lattice or a channel structure, where extrinsic structural means are provided to direct the object past the stations. Both electrically charged and neutral extended objects may be moved by these means.

In a more preferred embodiment, electrokinetic forces are used to move charged extended objects past the stations. In this case, the extended object is moved relative to the solvent, which results in self-orientation of extended objects with their long axes parallel to the direction of movement. Electrokinetic force is especially preferred to move DNA (electrophoresis), which has a negatively charged backbone. It has been shown that rod-shaped polyelectrolytes, and in particular nucleic acids, are polarized in an electric field (Eigen & Schwarz (1962) In "Electrolytes", Pergamon Press). This results in very large induced dipole moments in DNA, which with field strengths of $10^3$ V/cm leads to complete alignment of the molecule in the field. The relaxation time for the polarization is about one microsecond. This effect augments the effect of the moving solvent to help orient the DNA.

As a result of all of these effects, the DNA molecule is strongly oriented and stretched during gel electrophoresis (Bustamante (1991) Annu. Biophys. Biophys Chem. 20: 415–446; Holzwarth et al. (1989) Biopolymers 28: 1043–1058). Under typical electrophoretic conditions within a gel matrix in slab electrophoresis, the voltage is 5–50 V/cm and the velocity of short ($\leq$1000 base pairs) DNA fragments is $10^{-4}$–$10^{-5}$ m/s. When electrophoresis is performed in capillary-like structure where a small current cross-section facilitates efficient heat dissipation, voltages of up to 200–500 V/cm can be applied and the speed of the DNA molecule can reach $10^{-3}$ m/s.

Parameters of polymer movement through the disclosed devices can be optimized using theoretical models known in the art (Sung & Park (1996) Phys. Rev. Lett. 77: 783–786; Williams et al. (1998) Biophys. J. 75: 493–502).

In another preferred embodiment, polymers are moved by establishing a pressure head on the side where the polymers enter the sample device, encouraging fluid to flow to the far side of the sample device, opened to atmospheric pressure or maintained at reduced pressure. The pressure head may come from any device imposing a physical force, such as a syringe pump. In another embodiment of the pressure control system, in devices with a pressure drop of less than atmospheric pressure, one end of the system is pulled with a vacuum, literally sucking material to be analyzed through the sample device.

In another embodiment, a molecular motor can be used to guide an extended object past a station within interactive proximity of an agent selected from the group consisting of an electromagnetic radiation source, a quenching source, and a fluorescence excitation source. A molecular motor is a device that physically interacts with the extended object and pulls it past the station. Molecular motors include, but are not limited to DNA helicases, DNA polymerases, dyenin, myosin, actin, and kinesin. The molecular motor can be in a solution or positioned on a support. If the molecular motor is positioned on a support, it is not required that an agent is attached to the molecular motor. For example, the station may be created by the support itself, for instance, if the support is a conductance membrane. Alternatively, the station may be a separate entity attached to the support such that it is in interactive proximity with a polymer moving through the molecular motor. Molecular motors are described in more detail in PCT Publication No. WO 98/35012, in U.S. patent application Ser. No. 60/096,540 entitled "Molecular Motors," filed Aug. 13, 1998, and in U.S. patent application Ser. No. 09/374,414 entitled "Molecular Motors," inventor Eugene Y. Chan, filed of even date herewith, all of which are incorporated herein by reference in their entirety.

6. EXAMPLES

6.1 Example 1

Preparation of Sample Devices Having Fluorescent Dyes at the Stations

Preparation of High Molecular Weight Polyacrylamide Labeled With Fluorescein

A concentrated solution (20–40 mM) of succinimidyl ester of carboxyfluorescein (fluorescein SE) was prepared in DMF (dimethylformamide). A solution of allylamine ($H_2C=CH-CH_2-NH_2$) was prepared in 0.1 M sodium bicarbonate (pH=8.3). The concentrated solution of fluorescein SE in DMF was added to the allylamine solution such that the proportion of DMF in the final reaction mixture did not exceed 10% by weight, the final concentration of allylamine was 15 mM, and a 1.5–2 molar excess of the allylamine to the fluorescein SE was present in the final solution. The reaction proceeded for 1–2 hours in the dark at room temperature, and more than 80% of the fluorescent label was attached to the allylamine via the amino group.

A fluoroscein-labeled polyamide gel concentration was prepared as follows. After the reaction of fluorescein with allylamine, concentrated solutions of acrylamide (30% w/w) and electrophoretic buffer (10×TBE) are added directly to the reaction mixture. Actual volumes of the added solutions depend on the volume of reaction mixture and are determined from conditions that the final concentration of acrylamide is 5% w/w and final dilution of the buffer is 1×TBE. To initiate polymerization, 3 $\mu$l of TEMED and 30 $\mu$l of 10% ammonium persulfate were added. Polymerization was allowed to proceed for 5–7 hours at room temperature. The mixture was transferred to an Ultrafree-15 Protein Concentrator Unit (Millipore, Bedford, Mass.) with a molecular weight cutoff of 5,000 D. The concentrator was spun in a centrifuge at 2,000×g until less than 10% of the orginal volume of the gel was left on the membrane. The filtrate, containing non-reacted fluorophore and low molecular weight fractions of acrylamide, was discarded. The retentate was enriched in high molecular weight fractions of labeled acrylamide. TBE was added to the retentate until the original volume was restored. The purification of the labeled gel by centrifugation was repeated 5–6 times. More than 90% of the fluorescein was incorporated into the final labeled gel concentrate, which contained 1.8 mM fluorescein labeled acrylamide.

In order to prepare a polyacrylamide gel for FRET analysis with a desired amount of covalently linked fluorescein stations, a desired aliquot of the gel concentrate is added to a polymerizing gel mixture. The final concentration of the fluorophore in the polyacrylamide gel is limited by the condition that the average distance between the gel-bound stations should be larger than the maximal separation interval between the labels on the object to be analyzed.

Preparation of a Lattice of Non-Emitting Nanobeads With Distributed Fluorescent Beads A colloidal suspension of monodisperse polystyrene beads is prepared in water or a desired buffer solution (if the original suspension arrives at a concentration of <10% it should first be concentrated). Fluorescent beads are added at this stage and dispersed in the suspension by vortexing. The final concentration of the fluorescent centers within the lattice is limited by the condition that the average distance between the stations should be larger than the maximal separation interval between the labels on the object to be analyzed.

The colloidal suspension is transferred into a capillary tube (a flat capillary is preferred). A quasicrystallization process is performed by sedimentaion of the beads in a centrifuge at 200–800×g for several hours. The actual time for lattice growth depends upon the desired size of the quasicrystal and upon the diameter of the beads used. It can take up to several days to grow a quasicrystal that is several millimiters long.

Preparation of a Membrane With Nano-Channels and a Fluorescent Layer

As a prototype for the nanochannel system for the correlated FRET measurements, polycarbonate track-etch membranes (PCTE) is used (Osmonics, Livermore, Calif.). PCTE membranes are microporous screens that derive their special properties from the manufacturing technology. They are comprised of cylindrical pores of regular diameter that are normal (within ±35°) to the membrane surface. Pore diameters of 10 nm and larger are available. The distribution of actual diameters of the pores is narrow and varies from +0% to −20% of rated pore size. Typical pore densities can be as high as $10^9$ pores/cm$^2$.

A polycarbonate layer containing 0.4% pyrrometene 580 dye (Exciton, Dayton, Ohio) is cast onto a polycarbonate supporting film by a controlled-gap blade technique. Fluorescent layers with thickness of several hundreds of nanometers have been prepared in this way. Using spin coating, fluorescent layers with thickness of tens of nanometers are possible. After the deposition, the film is the sum of two layers, each of them mostly or completely made of polycarbonate. A general track-etch technique is applicable to such membranes (either in house or by order to Osmonics), resulting in a PCTE membrane with nanochannels and a fluorescent layer.

Alternatively, reactive groups (e.g., amino groups) are introduced onto the surface of a PCTE membrane with 10 nm channels by techniques known in the art, or such labeling is performed by order to Xenopore, Inc. (Hawthorne, N.J.). Afterwards, a dye is covalently linked to them, for example, the succinimidyl ester of Texas Red® can be used with amino groups.

6.2 Example 2

Calculation of Illumination Intensity Needed to Achieve a High FRET Signal to Noise Ratio The probability of energy transfer between donor and acceptor, $P_{tr}$, is determined by the Förster factor, and is ½ at the Förster distance $Z_F$. The overall number of FRET events, $N_{tr}$, that occur during $T_{tr}$, the time that donor and acceptor are within interaction proximity, is $$N_{tr}=P_{tr}X=P_{tr}X_0T_{tr} \qquad (3)$$

where X is the number of excitations of the donor center during $T_{tr}$, and $X_0$ is the number of excitations of the donor center per second. If $N_{tr} \geq 1$, the FRET probability is 1 and all FRET events are correlated (i.e. each FRET event has a corresponding correlated FRET event). If $N_{tr}<1$, then $N_{tr}=P^0{}_{tr}$, the overall probability of excitation transfer from a donor to an acceptor at a given illumination intensity. In this case, the probability of a correlated FRET event is $P_{corr}=(P^0{}_{tr})^2$. If $P_{corr}<1$, then the excess occurrence of background fluorescence over correlated fluorescence is given by: $F=P^0{}_{tr}/P_{corr}=1/P^0{}_{tr}$ per correlated photon.

In addition to these limitations, there are also limitations introduced by the type of apparatus used to measure the FRET. For example, the finite aperture of the optical system, reflections, and losses on filters decrease K, the overall proportion of registered photons. Therefore, the probability $P_{act}$ should be used instead of $P^0{}_{tr}$:

$$P_{act}=KP^0{}_{tr}=KP_{tr}X_0T_{tr} \qquad (4)$$

To measure $N_{corr}$, the number of correlated photons necessary for a high signal to noise ratio, overall $I_{tot}$ of the photons should be measured:

$$I_{tot}=2N_{corr}F=2N_{corr}/P_{act}=2N_{corr}/(KP_{tr}X_0T_{tr}) \qquad (5)$$

To achieve a large $N_{corr}$ within a reasonable time of measurement, T, the probability $P_{act}$ should be as close to unity as possible. However, the proportion of registered photons K is always <1 and non-correlated photons will be always present in excess of 1/K.

Losses in a system having custom made interference filters and a dichroic mirror total 40–50% due to reflection and absorption. Additional losses of 10–15% are introduced by the limited width (80 nm) of the bandpass filter in the emission channel. Collection efficiency for an aspheric lens (special design, fused silica, NA=0.88) is 0.0525. This results in K=(0.55)(0.85)(0.0525)=0.025=2.5% for this system. If a microscope objective (Plan-NEOFLUOAR, NA=1.3) is used instead of the aspheric lens, then K=(0.55)(0.85)(0.18)=0.084=8.4%. Furthermore, if PMT R943-02 (Hamamatsu) with GaAs photocathode having a quantum efficiency of detection >10% at wavelengths >840 nm is used, then the K value is further decreased to 0.0025 or 0.0084 for an aspheric lens or microscope objective, respectively. For further calculations, the value K=0.05 is used.

For δL=10 nm and a velocity of the extended object of V=$10^4$ nm/s, $T_{tr}=10^{-3}$s=1 ms. Assuming that the absorption cross-section of the donor center is σ=3×10$^{-16}$ cm$^2$, the quantum efficiency of donor center emission Q=0.5, and at an excitation wavelength of 488 nm (f=2.46×10$^{15}$ photons/s for 1 mW of power), the density of excitation power, $W_A$, needed to provide $N_{em}$ emitted photons within $T_{tr}$ can be estimated by:

$$W_A=N_{em}/(\sigma QT_{tr}f) \qquad (6)$$

For $N_{em}$=100 photons, an excitation density power of $W_A$=270 W/cm$^2$ is needed. If the illuminated spot diameter is 0.05 mm (such as that produced when using an aspheric lens), then an Ar laser having power of at least 5.3 mW in the 488 nm line may be used. Faster velocities of the extended object require even more power because $T_{tr}$ decreases. Use of a microscope objective lens increases the illumination density considerably due to a smaller illuminated spot diameter (microns). However, the maximum possible excitation intensity is limited by the photobleaching of donor center fluorophores (see, e.g. analysis in U.S. Pat. No. 4,979,824) and optimization of excitation intensity is a complex process.

It can reasonably be assumed that $X_0T_{tr}$=10–100 photons corresponds to an optimal level of illumination, which corresponds to a total emission of $10^4$–$10^5$ photons/sec perfluorophore, which results in bleaching within one second. Further assuming that $P_{tr}$=0.5 and using equation (5), $I_{tot}$=8×$10^4$ photons should be accumulated to measure $N_{corr}$=1000 photons for optimization of the signal to noise ratio.

6.3 Example 3

The Effects of Background Emission on FRET Measurements

The calculations performed thus far assume that donors and acceptors are ideal, that is, they are excited and emit within a finite spectral range only. In actuality, donor fluorophore emission peaks have low intensity shoulders or tails toward the red side of the peaks, while acceptor fluorophore excitation peaks have low intensity shoulders or tails toward the blue side of the peaks. Therefore, exciting donors will also directly excite acceptors to some extent. Furthermore, in addition to acceptor fluorescence, there is some emission from the donor at the same wavelengths.

Consider the dye pair fluorescein (donor) and Texas Red® (acceptor). Texas Red® emission has maximum at 611 nm. Although the maximum of fluorescein fluorescence is at 524 nm, it still has considerable emission (9% of its maximal value) at 611 nm. If the Ar laser line at 488 nm is used to excite the fluorescein, it would also directly excite Texas Red®, although with an efficiency of 2.5% of the maximal value. Another choice of donor can be Alexa™ 488. On the one hand, its emission spectrum has less overlap with the excitation spectrum of Texas Red®, which makes FRET less efficient than from fluorescein, provided all other conditions are the same. On the other hand, Alexa™ 488 emission at 611 nm is only 2% of its maximal value and it is excited more efficiently than fluorescein at 488 nm. Alexa™ 488 is also much more photostable than fluorescein. Therefore, the combination of factors makes Alexa™ 488 a more preferred donor for the applications herein.

Experiments have been performed on the energy transfer between the fluorescein (donor) and YOYO-3 iodide (acceptor, Molecular Probes, OR). Fluorescein was bound covalently to a polyacrylamide gel (5% gel with 0.003% [mol/mol] of fluorescein labeled monomers, see more details below). Short fragments of DNA (100 to 1000 base pairs) were run through the gel in an amount of 50 to 150 nanograms per fraction. The DNA was labeled with YOYO-3 iodide, which binds to double-stranded DNA (1:10 of YOYO-3:DNA base pairs) and has a very small fluorescence quantum yield in its unbound form. Fluorescence was monitored at 641 nm, where $I_{em}(641)$ is 3.8% of $I_{em}$max for fluorescein. The $I_{ex}(488)$ of YOYO-3 is 1.4% of the $I_{ex}$max. Under these conditions, detected fluorescein emission at 641 nm was $1.3 \times 10^6$ photons/s while YOYO-3 emission was $3 \times 10^4$ photons/s. More than 90% of YOYO-3 emission was due to FRET. The proportion of the YOYO-3 emission due to direct excitation and due to FRET was calculated by comparison of the emission of YOYO-3 excited at 488 and 580 nm in presence and absence of fluorescein, respectively. Fluorescein emission is not excited at 580 nm.

For the tested system, the donor fluorescence was 43 times larger than the overall acceptor fluorescence and the fluorescence of the directly excited acceptor was only a minor fraction of the FRET-induced acceptor emission. For this experimental configuration and dye pair, results could be improved by increasing the concentration of moving acceptors and decreasing the concentration of donor centers. For an inverted system, where the donor is attached to DNA and the acceptor is immobilized in a spatial network, the opposite concentration ratio would be more advantageous. The actual concentrations of D or A and their placement should be chosen for each dye pair according to the spectral and physico-chemical properties of the molecules. The use of Alexa 488 in place of fluorescein in this system decreases the donor fluorescence at 641 nm to $4 \times 10^5$ photons/s.

Other factors contribute to the generation of background signal during FRET measurements. Among the most important of these are Rayleigh and Raman scattering, which are due to solvent and other materials constituting the system. The contribution of Rayleigh and Raman scattering to background signal is approximately proportional to the illuminated volume used in the experiment. For the smallest volume, several femtoliters, tested for direct dye emission, a S/N ratio of 40 was observed. With suppression of the rotational Raman bands of water, the S/N ratio was reported to be as high as 1700 (Eigen & Rigler (1994) Proc. Natl. Acad. Sci. U.S.A. 91: 5740–5747). In the experiments performed herein, the scattering contribution to the background is less substantial because the emission is measured at a wavelength that is more than 100 nm from the excitation wavelength, and background signal due to scattering is filtered out with donor emission background.

6. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for analyzing extended objects comprising:
   (a) moving with respect to at least a first station a plurality of similar extended objects that are each similarly labeled at similar positions with at least a first unit-specific marker and a second unit-specific marker to generate a plurality of object-dependent impulses as the similar extended objects pass the first station, wherein the first and second unit-specific markers are at different positions along each similar extended object, wherein the similar extended objects are extended molecules or extended molecular complexes;
   (b) measuring the generated plurality of object-dependent impulses as a function of time, wherein the object-dependent impulses generated due to said first unit-specific marker of an individual one of said plurality of similar extended objects passing said first station and said object-dependent impulses generated due to said second unit-specific marker of said individual one of said plurality of similar extended objects passing said first station are resolved in time; and
   (c) calculating an autocorrelation function of said measured plurality of object-dependent impulses, to analyze the extended objects.

2. The method of claim 1 wherein said plurality of similar extended objects are moved with respect to the first station at similar velocities.

3. The method of claim 1, wherein the plurality of similar extended objects is a plurality of polymers.

4. The method of claim 3, wherein each polymer in the plurality of polymers is identical to every other polymer in the plurality of polymers.

5. The method of claim 4, wherein each polymer in the plurality of polymers is labeled with identical unit-specific markers at identical positions within the polymer.

6. The method of claim 3, 4 or 5, wherein each polymer in the plurality of polymers is a nucleic acid.

7. The method of claim 6, wherein the nucleic acid is DNA.

8. The method of claim 1, wherein the autocorrelation function is defined by the formula:

$$G(\tau) = 1/T \int_0^T I(t)I(t+\tau)dt$$

where $G(\tau)$ is the autocorrelation function of the time dependence of measured object-dependent impulses, T is the total time of measurement of I(t), and I(t) is the object-dependent impulse measurement at each time point t.

9. The method of claim 1, wherein the autocorrelation function is defined by the formula:

$$G_j = (1/N)\sum_{i=0}^{N} I_i I_{i+j}$$

where $G_j$ is the autocorrelation function of the time dependence of measured object-dependent impulses at time $j\Delta t$, N is the total number of data values, $I_i$ is the object-dependent impulse measurement at time $t_i$, $I_{i+j}$ is the object-dependent impulse measurement at time $t_i+j\Delta t$, and $\Delta t$ is a time interval.

10. The method of claim 1, wherein the at least a first station is a plurality of stations.

11. The method of claim 10, wherein the plurality of similar extended objects is moved through a lattice of beads and the plurality of stations is positioned on a subset of the plurality of beads.

12. The method of claim 8, 9 or 11, wherein the plurality of similar extended objects is a plurality of polymers.

13. The method of claim 12, wherein each polymer in the plurality of polymers is a nucleic acid.

14. The method of claim 13, wherein the nucleic acid is DNA.

15. The method of claim 10, wherein the plurality of similar extended objects is moved through a channel, said channel having a first end, a second end, and at least one wall, the plurality of stations being positioned along the at least one wall.

16. The method of claim 10, wherein the plurality of similar extended objects is moved through a channel, said channel having a first end, a second end, and at least one wall, the plurality of stations being positioned at said first end or said second end.

17. The method of claim 15 or 16, wherein the plurality of similar extended objects is a plurality of polymers.

18. The method of claim 17, wherein each polymer in the plurality of polymers is a nucleic acid.

19. The method of claim 18, wherein the nucleic acid is DNA.

20. The method of claim 10, wherein the plurality of similar extended objects is moved simultaneously through a plurality of channels, each channel in said plurality of channels having a first end, a second end, and at least one wall, each channel having at least one station positioned along the at least one wall.

21. The method of claim 10, wherein the plurality of similar extended objects is moved simultaneously through a plurality of channels, each channel in said plurality of channels having a first end, a second end, and at least one wall, each channel having at least one station positioned at said first end or said second end.

22. The method of claim 20 or 21, wherein the plurality of similiar extended objects is a plurality of polymers.

23. The method of claim 22, wherein each polymer in the plurality of polymers is a nucleic acid.

24. The method of claim 23, wherein the nucleic acid is DNA.

25. The method of claim 1, wherein the plurality of similar extended objects is moved through the action of at least one molecular motor.

26. The method of claim 25, wherein the at least one molecular motor is a plurality of molecular motors in solution.

27. The method of claim 25 or 26, wherein the plurality of similar extended objects is a plurality of polymers.

28. The method of claim 27, wherein each polymer in the plurality of polymers is a nucleic acid.

29. The method of claim 28, wherein the nucleic acid is DNA.

30. The method of claim 1, wherein the object-dependent impulses generated due to said first unit-specific marker of an individual one of said plurality of similar extended objects passing said first station and said object-dependent impulses generated due to said second unit-specific marker of said individual one of said plurality of similar extended objects passing said first station are different.

31. The method of claim 30, wherein the plurality of similar extended objects is a plurality of polymers.

32. The method of claim 31, wherein each polymer in the plurality of polymers is a nucleic acid.

33. The method of claim 32, wherein the nucleic acid is DNA.

34. The method of claim 1 wherein the object-dependent impulses are fluorescence resonance energy transfer.

35. The method of claim 34, wherein said first station comprises at least one donor fluorophore and said first unit-specific marker and said second unit-specific marker each comprise at least one acceptor fluorophore.

36. The method of claim 34, wherein said first station comprises at least one acceptor fluorophore and said first unit-specific marker and said second unit-specific marker each comprise at least one donor fluorophore.

37. The method of claim 34, 35 or 36, wherein the plurality of similar extended objects is a plurality of polymers.

38. The method of claim 37, wherein each polymer in the plurality of polymers is a nucleic acid.

39. The method of claim 38, wherein the nucleic acid is DNA.

40. The method of claim 1, wherein repetitive information in the measured plurality of object-dependent impulses provides information about the length of the extended objects.

41. The method of claim 1, wherein analysis of the extended objects provides information about the distance between said first unit-specific marker and said second unit-specific marker on the extended objects.

42. The method of claim 2, wherein analysis of the extended objects provides information about the velocity of the extended objects.

43. The method of claim 1, wherein analysis of the extended objects provides information about the linear arrangement of units within the extended objects.

44. The method of claim 40, 41, 42 or 43, wherein the plurality of extended objects is a plurality of polymers.

45. The method of claim 44, wherein each polymer in the plurality of polymers is a nucleic acid.

46. The method of claim 45, wherein the nucleic acid is DNA.

47. A method for analyzing extended objects comprising calculating an autocorrelation function of measured object-dependent impulses, wherein said object dependent impulses have been produced by:

(a) moving with respect to at least a first station a plurality of similar extended objects that are each similarly labeled at similar positions with at least a first unit-specific marker and a second unit-specific marker to generate a plurality of object-dependent impulses as the similar extended objects pass the first station, wherein the first and second unit-specific markers are at different positions along each similar extended object, wherein the similar extended objects are extended molecules or extended molecular complexes; and (b) measuring the generated plurality of object-dependent impulses as a function of time, wherein the object-dependent impulses generated due to said first unit-specific marker of an individual one of said plurality of similar extended objects passing said first station and said object-dependent impulses generated due to said second unit-specific marker of said individual one of said plurality of similar extended objects passing said first station are resolved in time.

48. The method of claim 47, wherein the extended objects are polymers.

49. The method of claim 48 wherein the polymers are nucleic acids.

50. The method of claim 49, wherein the nucleic acids are DNA.

51. The method of claim 47, wherein the autocorrelation function is defined by the formula:

$$G(\tau) = 1/T \int_0^T I(t)I(t+\tau)dt$$

where $G(\tau)$ is the autocorrelation function of the time dependence of measured object-dependent impulses, T is the total time of measurement of I(t), and I(t) is the object-dependent impulse measurement at each time point t.

52. The method of claim 47, wherein the autocorrelation function is defined by the formula:

$$G_j = (1/N)\sum_{i=0}^{N} I_i I_{i+j}$$

where $G_j$ is the autocorrelation function of the time dependence of measured object-dependent impulses at time $j\Delta t$, N is the total number of data values, $I_i$ is the object-dependent impulse measurement at time $t_i$, $I_{i+j}$ is the object-dependent impulse measurement at time $t_i+j\Delta t$, and $\Delta t$ is a time interval.

53. The method of claim 47, wherein the object-dependent impulses generated due to said first unit-specific marker of an individual one of said plurality of similar extended objects passing said first station and said object-dependent impulses generated due to said second unit-specific marker of said individual one of said plurality of similar extended objects passing said first station are different.

54. The method of claim 53, wherein the extended objects are polymers.

55. The method of claim 51, 52 or 54, wherein the polymers are nucleic acids.

56. The method of claim 55, wherein the nucleic acids are DNA.

57. The method of claim 47 wherein the object-dependent impulses are fluorescence resonance energy transfer.

58. The method of claim 57, wherein the extended objects are polymers.

59. The method of claim 58, wherein the polymers are nucleic acids.

60. The method of claim 59, wherein the nucleic acid is DNA.

61. The method of claim 47, wherein the analysis of the extended objects provides information about the length of the extended objects.

62. The method of claim 47, wherein analysis of the extended objects provides information about the distance between said first unit-specific marker and said second unit-specific marker on the extended objects.

63. The method of claim 47, wherein analysis of the extended objects provides information about the velocity of the extended objects.

64. The method of claim 47, wherein analysis of the extended objects provides information about the linear arrangement of units within the extended objects.

65. The method of claim 61, 62, 63 or 64, wherein the extended objects are polymers.

66. The method of claim 65, wherein the polymers are nucleic acids.

67. The method of claim 66, wherein the nucleic acids are DNA.

* * * * *